United States Patent
Chen

(10) Patent No.: US 11,378,090 B2
(45) Date of Patent: *Jul. 5, 2022

(54) COMPACT CENTRIFUGAL PUMP WITH MAGNETICALLY SUSPENDED IMPELLER

(71) Applicant: CH BIOMEDICAL (USA) INC., Torrance, CA (US)

(72) Inventor: Chen Chen, Santa Barbara, CA (US)

(73) Assignee: CH BIOMEDICAL (USA) INC., Torrance, CA (US)

( * ) Notice: Subject to any disclaimer, the term of this patent is extended or adjusted under 35 U.S.C. 154(b) by 111 days.

This patent is subject to a terminal disclaimer.

(21) Appl. No.: 17/116,451

(22) Filed: Dec. 9, 2020

(65) Prior Publication Data
US 2021/0172449 A1    Jun. 10, 2021

Related U.S. Application Data

(63) Continuation of application No. 16/032,316, filed on Jul. 11, 2018, now Pat. No. 10,947,986.

(51) Int. Cl.
*F04D 29/048* (2006.01)
*A61M 1/10* (2006.01)
(Continued)

(52) U.S. Cl.
CPC ......... *F04D 29/048* (2013.01); *A61M 60/419* (2021.01); *A61M 60/82* (2021.01);
(Continued)

(58) Field of Classification Search
CPC .......... H02K 5/112; H02K 5/132; H02K 5/12; H02K 49/106; H02K 49/104; H02K 7/09;
(Continued)

(56) References Cited

U.S. PATENT DOCUMENTS 5,044,897 A * 9/1991 Dorman ................ F04D 13/064
  417/365
5,112,202 A * 5/1992 Oshima ................ A61M 60/422
  417/423.1
(Continued)

FOREIGN PATENT DOCUMENTS

CN    1347585 A    5/2002
CN    1886161 A    12/2006
(Continued)

OTHER PUBLICATIONS

Japanese Office Action for Application No. 2019007033 dated Sep. 2, 2020, 11 pages.
(Continued)

*Primary Examiner* — Kenneth J Hansen
*Assistant Examiner* — Benjamin Doyle
(74) *Attorney, Agent, or Firm* — Seyfarth Shaw LLP

(57) ABSTRACT

A centrifugal fluid pump with a fully magnetically suspended rotor to improve blood compatibility when pumping blood is disclosed. The pump stabilizes radial displacements of a disc-like rotor with active control through separate electric motor and magnetic bearings to improve the pump's critical performances including device packaging size, system simplicity and reliability, stiffness and other dynamic performances of suspension, power efficiency, and others.

27 Claims, 24 Drawing Sheets

(51) Int. Cl.
*F04D 13/06* (2006.01)
*F16C 32/04* (2006.01)
*H01F 7/16* (2006.01)
*H02K 7/14* (2006.01)
*H02K 49/10* (2006.01)
*H02K 7/09* (2006.01)
*H02K 5/12* (2006.01)
*A61M 60/82* (2021.01)
*A61M 60/419* (2021.01)

(52) U.S. Cl.
CPC ........ *F04D 13/0653* (2013.01); *F16C 32/048* (2013.01); *H01F 7/1607* (2013.01); *A61M 2205/3365* (2013.01); *F16C 2360/44* (2013.01); *H02K 5/12* (2013.01); *H02K 7/09* (2013.01); *H02K 7/14* (2013.01); *H02K 49/104* (2013.01); *H02K 49/106* (2013.01)

(58) Field of Classification Search
CPC ..... H02K 7/14; A61M 1/1015; A61M 1/1036; A61M 2205/3365; F04D 13/0653; F04D 29/048; H01F 7/1607; F16C 32/048; F16C 2360/44
USPC .......................................................... 417/420
See application file for complete search history.

(56) References Cited

U.S. PATENT DOCUMENTS

| | | | | |
|---|---|---|---|---|
| 5,205,721 A * | 4/1993 | Isaacson | .................. | H02K 3/28 417/423.1 |
| 5,736,800 A * | 4/1998 | Iannello | ............... | F16C 32/048 310/90 |
| 5,840,070 A * | 11/1998 | Wampler | ............... | H02K 41/03 417/423.1 |
| 6,015,272 A * | 1/2000 | Antaki | ..................... | H02K 7/14 417/423.12 |
| 6,053,705 A | 4/2000 | Schob et al. | | |
| 6,074,180 A * | 6/2000 | Khanwilkar | ........ | A61M 60/422 417/420 |
| 6,155,969 A | 12/2000 | Schima et al. | | |
| 6,201,329 B1 | 3/2001 | Chen | | |
| 6,244,835 B1 * | 6/2001 | Antaki | ................ | A61M 60/422 417/423.1 |
| 6,394,769 B1 * | 5/2002 | Bearnson | ............ | A61M 60/419 417/423.12 |
| 6,589,030 B2 * | 7/2003 | Ozaki | ................. | F04D 13/0666 417/44.1 |
| 6,617,720 B1 * | 9/2003 | Egan, III | ............... | H02K 5/132 310/67 R |
| 7,112,903 B1 | 9/2006 | Schob | | |
| 7,229,258 B2 * | 6/2007 | Wood | .................... | A61M 60/82 417/423.15 |
| 7,416,525 B2 * | 8/2008 | Wampler | ............. | F04D 29/047 600/16 |
| 7,467,930 B2 * | 12/2008 | Ozaki | ................ | F04D 13/0666 417/423.12 |
| 7,976,271 B2 | 7/2011 | LaRose et al. | | |
| 8,088,059 B2 | 1/2012 | Jarvik | | |
| 8,282,359 B2 * | 10/2012 | Ayre | .................. | A61M 60/205 417/43 |
| 8,288,906 B2 * | 10/2012 | Onuma | ................ | F16C 32/048 310/216.099 |
| 8,378,543 B2 | 2/2013 | Filatov | | |
| 8,596,999 B2 | 12/2013 | Shinshi et al. | | |
| 9,091,271 B2 * | 7/2015 | Bourque | ............... | A61M 60/40 |
| 9,427,510 B2 * | 8/2016 | Siebenhaar | ........... | F04D 29/426 |
| 9,492,599 B2 * | 11/2016 | Schimpf | ............. | A61M 60/419 |
| 9,512,852 B2 * | 12/2016 | Wampler | ........... | F04D 29/2266 |
| 9,616,157 B2 * | 4/2017 | Akdis | ................... | F04D 29/048 |
| 9,623,161 B2 * | 4/2017 | Medvedev | ........... | A61M 60/50 |
| 9,638,202 B2 * | 5/2017 | Ozaki | ................... | A61M 60/40 |
| 9,683,601 B2 | 6/2017 | Filatov | | |
| 9,850,906 B2 * | 12/2017 | Ozaki | .................... | H02K 5/128 |
| 9,945,418 B1 * | 4/2018 | Allaire | .................... | H02K 7/09 |
| 10,245,361 B2 * | 4/2019 | Yanai | ..................... | F04D 29/426 |
| 10,371,152 B2 * | 8/2019 | Yanai | .................. | F04D 13/0666 |
| 10,543,301 B2 * | 1/2020 | Timms | ................. | A61M 60/419 |
| 2002/0012594 A1 * | 1/2002 | Ozaki | ................ | F04D 13/0666 417/423.12 |
| 2002/0105241 A1 * | 8/2002 | Carroll | .................... | H02K 7/09 310/90.5 |
| 2007/0280841 A1 * | 12/2007 | LaRose | ............... | A61M 60/871 417/423.12 |
| 2008/0240947 A1 * | 10/2008 | Allaire | ................ | F16C 32/0448 417/420 |
| 2012/0095280 A1 * | 4/2012 | Timms | ................. | F04D 29/048 600/16 |
| 2012/0156071 A1 * | 6/2012 | Hijikata | ................ | F04D 29/605 417/423.12 |
| 2014/0062239 A1 * | 3/2014 | Schoeb | ............... | F16C 32/0461 310/90.5 |
| 2015/0087889 A1 * | 3/2015 | Takatani | ............. | F16C 32/0408 600/16 |
| 2015/0330444 A1 * | 11/2015 | Wang | .................. | F16C 32/0485 310/90.5 |
| 2015/0361987 A1 * | 12/2015 | Lin | ........................ | F04D 29/048 417/420 |
| 2017/0040868 A1 * | 2/2017 | Noh | ........................ | H02K 21/44 |
| 2018/0252228 A1 * | 9/2018 | Henseler | ............... | F04D 29/048 |
| 2019/0199186 A1 * | 6/2019 | Noh | ........................ | H02K 21/20 |
| 2019/0356195 A1 * | 11/2019 | Holenstein | ............... | H02K 3/18 |
| 2020/0018318 A1 * | 1/2020 | Chen | ....................... | H01F 7/1607 |

FOREIGN PATENT DOCUMENTS

| | | |
|---|---|---|
| CN | 101415950 A | 4/2009 |
| CN | 101682229 A | 3/2010 |
| CN | 101927038 A | 12/2010 |
| CN | 102743803 A | 10/2012 |
| CN | 106574628 A | 4/2017 |
| CN | 106794293 A | 5/2017 |
| EP | 0899855 A1 | 3/1999 |
| EP | 1073844 B1 | 12/2012 |
| JP | 956812 A | 3/1997 |
| JP | 2005121157 A | 5/2005 |
| JP | 2007506027 | 3/2007 |
| JP | 2013536021 | 9/2013 |
| JP | 6011746 | 10/2016 |
| JP | 2017518159 | 7/2017 |
| WO | 2014140282 A1 | 9/2014 |

OTHER PUBLICATIONS

Chinese Office Action for Application No. 201910626615.8 dated Aug. 21, 2020, 8 pages.
Japanese Office Action for Application No. 2019007033 dated Dec. 4, 2019, 12 pages.
European Search Report for Application No. 19156840.1 dated Dec. 11, 2019, 8 pages.
Chinese Office Action for corresponding Chinese Application No. 201910626615.8 dated May 19, 2021, 5 pages.

* cited by examiner

COMPACT CENTRIFUGAL PUMP WITH MAGNETICALLY SUSPENDED IMPELLER

CROSS REFERENCES TO RELATED APPLICATIONS

This application is a continuation of, and claims the benefit to, U.S. patent application Ser. No. 16/032,316, filed Jul. 11, 2018, the contents of which are incorporated herein by reference in its entirety.

FIELD OF INVENTION

The present invention relates to pumps for handling fluids such as blood that are sensitive to mechanical stress. More particularly, the present invention relates to centrifugal pumps in which an impeller is suspended and rotated using magnetic fields without mechanical contact between the impeller and the pump housing.

BACKGROUND

Various types of rotary blood pumps have been developed for clinical use as either implantable or extracorporeal devices. Implantable blood pumps, also known as ventricular assist devices, are used for saving lives of heart failure patients. Some extracorporeal blood pumps are used for temporary ventricular assist, and others are an integral part of the heart-lung system during open-heart surgery, or part of the extracorporeal membrane oxygenator (ECMO) that provides life support for patients with heart and lung dysfunctions. One particular challenge in the design of these pumps pertains to the fact that blood cells and proteins in blood are prone to damage due to non-physiological flow in the pump, leading to hemocompatibility issues including hemolysis (broken red blood cells) and thrombosis (clotting of blood). In addition, implantable blood pumps may be miniaturized to lessen invasiveness of surgical implantation. These pumps need to be highly reliable since they are life-saving devices, and need high power efficiency to prolong the time interval between changes of the carry-on batteries.

How the pump impeller is suspended may have a significant impact on the pump's performance in handling blood or other stress-sensitive fluids. Three types of impeller suspension are known, including mechanical, hydrodynamic and magnetic suspension. Mechanical suspension relies on physical contact between the rotor and stationary part in the pump housing. A typical design of a mechanical suspension impeller can be found in U.S. Pat. No. 8,088,059 which incorporates a pair of mechanical bearings immersed in blood. Another design can be found in U.S. Pat. No. 6,155,969 where the entire suspension consists of a mechanical bearing (pivot bearing) and a magnetic bearing with permanent magnets. Although simple in construction, mechanical suspension is associated with blood damage due to excessive shear stress in the flow field near the bearing and heat generation on the bearing surfaces. Mechanically suspended impellers also suffer from durability issues due to mechanical wear of the bearing surfaces.

Apart from mechanical suspension, hydrodynamic suspension relies on localized pressures in a thin layer of fluid film, blood film in the case of a blood pump, that keeps the bearing couple separated. The bearing couple surfaces are specially designed so that when the rotor moves to a speed beyond a threshold, localized high pressure is established in the fluid filling in between the bearing couple. A typical blood pump with hydrodynamic suspension is described in U.S. Pat. No. 7,976,271 in which the hydrodynamic suspension is accompanied by a set of permanent magnetic suspensions to achieve full stability in all degrees-of-freedom. Although hydrodynamic suspension avoids direct physical contact, the suspension gap must be extremely small to maintain high enough localized pressure. This induces excessive shear stress in the flow field within the gap, which may cause damage to the blood or other stress-sensitive fluid in the gap to a comparable extent as that of a mechanical bearing.

Magnetic suspension differs from mechanical or hydrodynamic suspension by employing a magnetic force, which is inherently non-contact, eliminating the need for a fluid as a medium to suspend the pump impeller. It has been demonstrated that a rotor can be fully suspended with desired stiffness in all degrees-of-freedom by using actively controlled electromagnets alone or in combination with permanent magnets. Unlike hydrodynamic suspension, magnetic suspension allows a significantly greater suspension gap so that blood in the gap is subjected to less shear stress, which helps to improve blood compatibility. Another advantage of magnetic suspension is the lack of physical contact between the components, eliminating any mechanical wear on the parts of the suspension.

Pumps capable of handling stress sensitive fluids without mechanical wear may be implemented in other applications aside from pumping blood. For example, chemical-mechanical planarization (CMP) using a slurry of precise particles is a common process for polishing a wafer surface in the integrated circuit industry. It has been observed that excessive stress in slurry mixtures during transportation causes aggregation of the suspended particles, and the oversized particles lead to defect scratches on the wafer surface. This issue can be addressed by replacing the diaphragm pump in the conventional process with a fully magnetically suspended pump that can avoid excessive stress in the slurry. Another area of application pertains to transportation of ultra-pure fluids, e.g. ultra-pure water for manufacturing of microelectronic components. Using full magnetic suspension the mechanical wear inside the pump can be reduced and thusly avoid contamination of wear-off debris into the pure fluid.

The rotor in a magnetically suspended pump can be classified into shaft-like and disc-like types. A shaft-like rotor has greater axial dimension than radial dimension and is usually suspended with two sets of radial/journal bearings that are distinctly separated along the rotor's rotational axis. A disc-like rotor has greater radial dimension than axial dimension or may have substantially similar axial and radial dimensions and is usually suspended with a single set of radial bearing. Inclination of a shaft-like rotor is usually stabilized with a torque resulting from the difference in the radial bearing forces that are apart from each other along the shaft axis. Conversely, inclination of a disc-like rotor is usually stabilized with the overall effect of the distributed forces on the rotor which results in a net torque about the inclination axes. The distributed forces may be provided by a special tilt bearing unit arranged around the rotor, or by a single unit of magnetic bearing that serve the dual functions of radial and tilt suspension.

SUMMARY

Embodiments of the present invention include a pump with a fully magnetically suspended rotor to improve blood compatibility when pumping blood, or other fluid with similar fluid dynamic characteristics. In particular, it is desirable to have such a pump that stabilizes radial displacements of a disc-like rotor with active control through separate electric motor and magnetic bearings to improve the pump's critical performances including device packaging size, system simplicity and reliability, stiffness and other dynamic performances of suspension, power efficiency, and others.

One embodiment of the invention includes a pump apparatus with a housing having inlet and outlet for respectively receiving and discharging fluid and a central axis. A rotor may be positioned within the interior of the housing to be rotatable about the central axis. The rotor may have an impeller for pumping fluid between the inlet and the outlet, and may be magnetically suspended to maintain a flow channel between the rotor and the housing. An electric motor may be adapted to drive the rotor about a rotational axis substantially coincident with the central axis. The electric motor may include a motor rotor assembly disposed within the rotor and a motor stator assembly disposed within the housing. The pump apparatus may further include a magnetic suspension device including an annular rotor primary pole piece mounted within the rotor coaxially with the rotational axis. The annular rotor primary pole piece may comprise a ferromagnetic material for channeling magnetic flux and have a first end surface, a second end surface, and a cylindrical side surface configured to serve as a rotor pole face. A plurality of electromagnet units mounted within the housing and circumferentially distributed at regular intervals about the central axis. Each electromagnet unit may include a pole shoe having a first end surface, a second end surface, and a side cylindrical surface configured to serve as a casing pole face. An iron core may extend from the pole shoe and a back yoke may connect two or more of the iron cores of different electromagnet units together. A coil may be wound around the iron core for conducting electric current. The pole shoe, iron core, and back yoke may comprise ferromagnetic material for channeling magnetic flux and the first end surface of the rotor primary pole piece and the first end surfaces of all the pole shoes are on a same side along an axial direction. The rotor pole face and each casing pole face may oppose to each other and define a primary suspension gap therebetween. The primary suspension gaps may be axially aligned with each other and circumferentially separated from each other.

At least one permanent magnet may generate a plurality of bias magnetic fluxes. Each bias magnetic flux may radially pass through one of the primary suspension gaps, and pass through the interior of the rotor primary pole piece and of the pole shoe of electromagnet unit. The at least one permanent magnet may be magnetized in such a direction that all the bias magnetic fluxes pass through the primary suspension gaps in a same polar direction. A plurality of position sensors may be disposed circumferentially around the rotor and mounted within the housing for detecting a radial position of the rotor pole face.

The pump apparatus may further include a feedback control system for generating and delivering electric current into the coils of the plurality of electromagnet units according to a real-time output of the position sensors. The feedback control system may include a control strategy adapted to achieve stability of radial positioning of the rotor. The plurality of the electromagnet units may be electrically and magnetically connected to jointly generate a modulating magnetic flux for active control of the position of the rotor along any one of two orthogonal radial axes. A first radial axis may have a first side and a second side divided by a second radial axis. The modulating magnetic flux may radially pass through a plurality of the primary suspension gaps and superimpose the bias magnetic fluxes to enhance the bias magnetic flux in the primary suspension gap located on the first side of the radial axis and to weaken the bias magnetic flux in the primary suspension gap located on the second side of the radial axis.

BRIEF DESCRIPTION OF THE DRAWINGS

For the purpose of facilitating an understanding of the subject matter sought to be protected, there are illustrated in the accompanying drawings embodiments thereof, from an inspection of which, when considered in connection with the following description, the subject matter sought to be protected, its construction and operation, and many of its advantages should be readily understood and appreciated.

DETAILED DESCRIPTION

Figure 1:
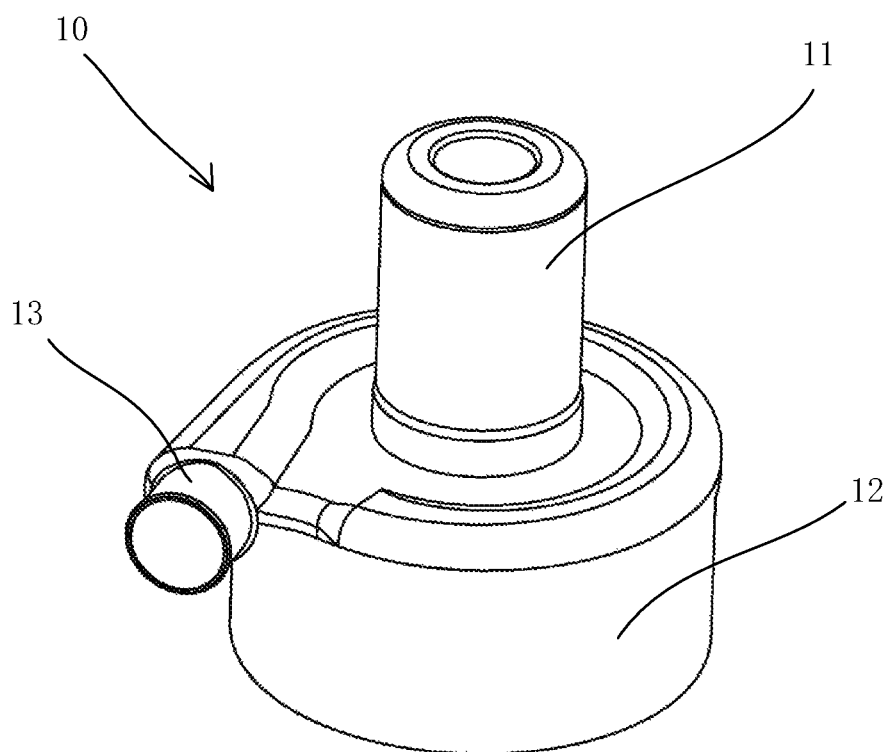
FIG. 1 is a top front perspective of a pump in accordance with an embodiment the present invention.

While this disclosure is susceptible of embodiments in many different forms, there is shown in the drawings, and will herein be described in detail, certain embodiments with the understanding that the present disclosure is to be considered as an exemplification of the principles of the disclosure and is not intended to limit the broad aspect of the disclosure to embodiments illustrated.

Figure 2:
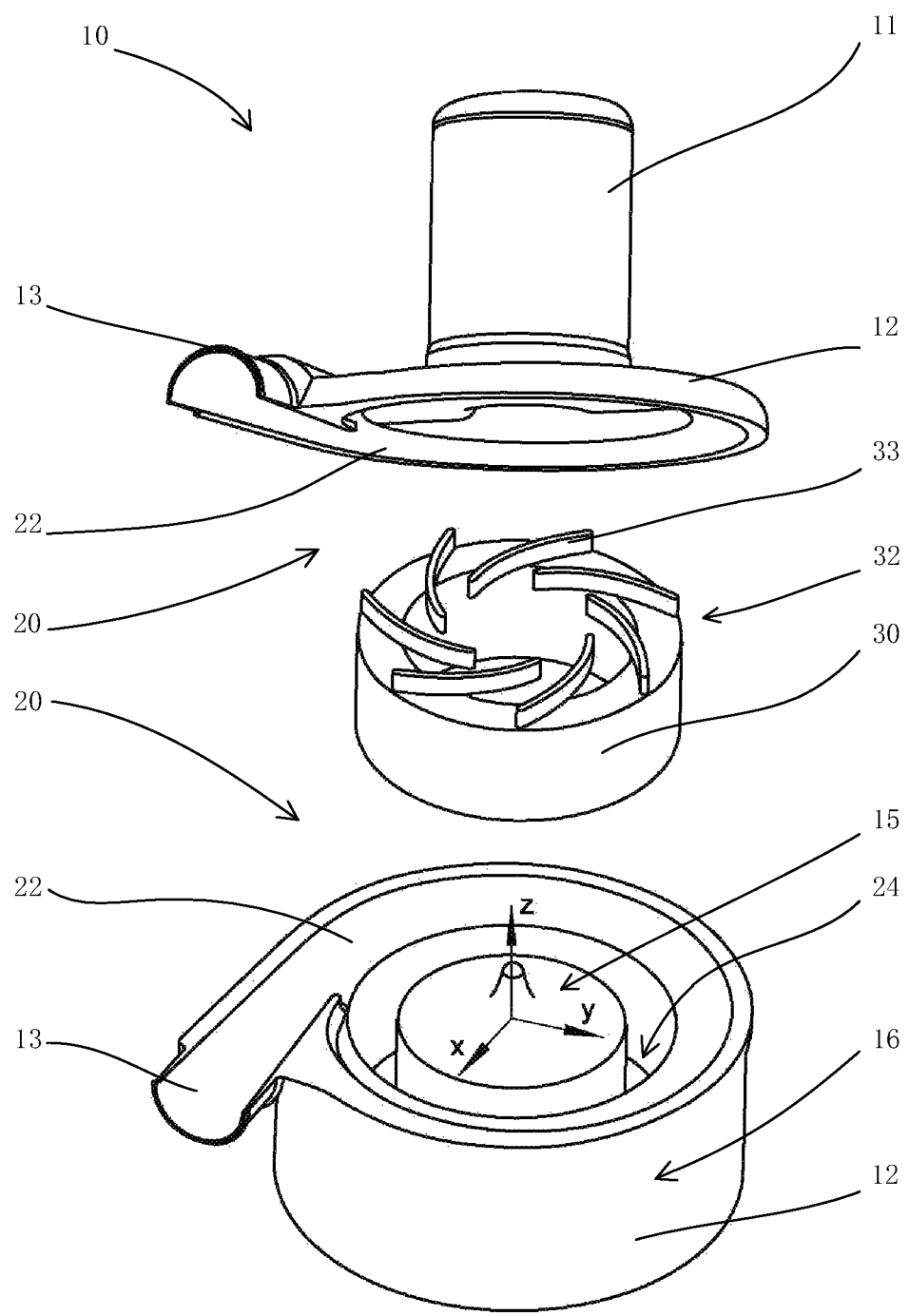
FIG. 2 is an exploded view of the pump of FIG. 1, showing the pump's interior construction for fluid flow through the pump in accordance with an embodiment the present invention.
Figure 3:
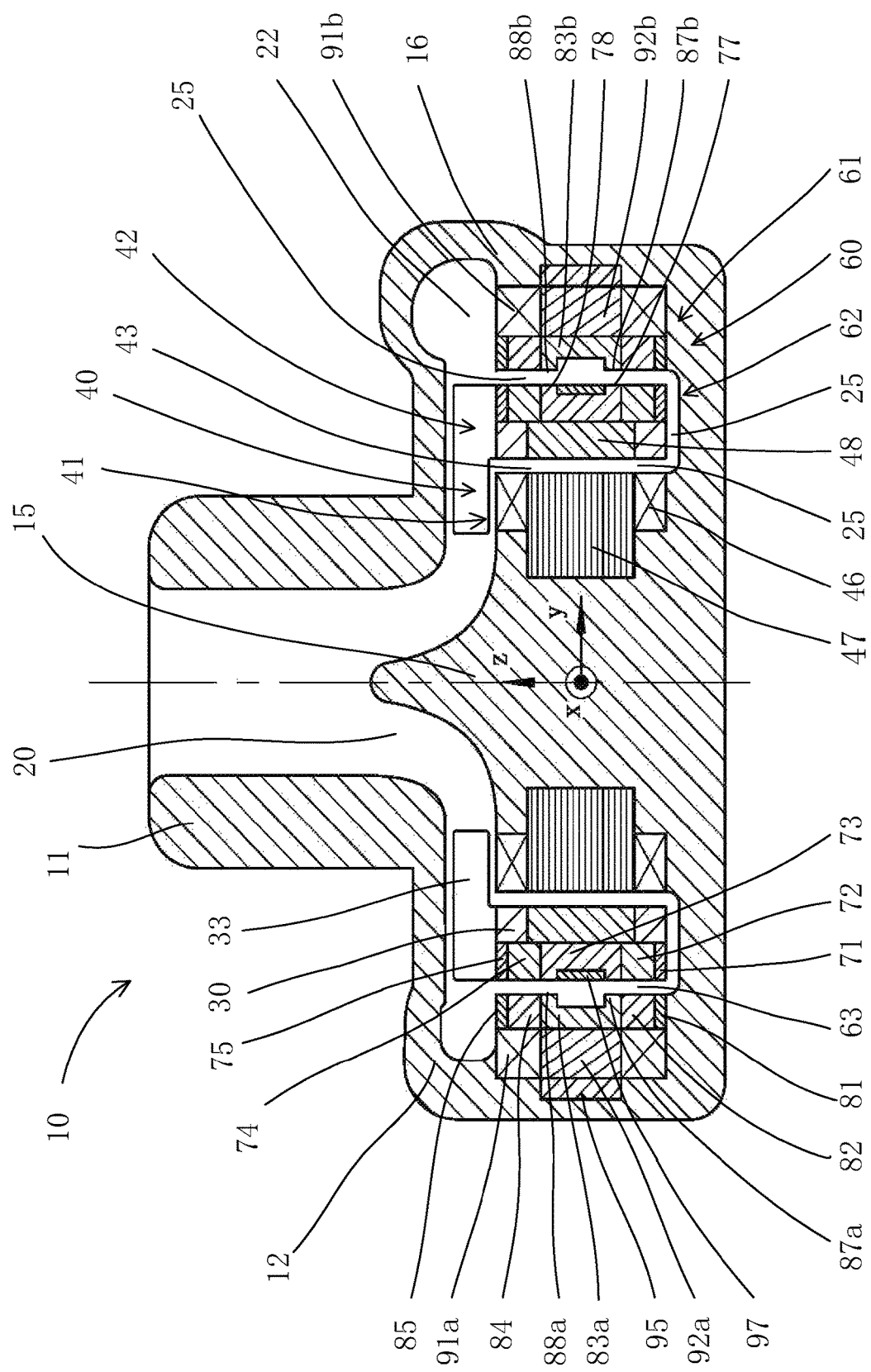
FIG. 3 is a front cross-sectional view of the pump of FIG. 1 in accordance with an embodiment the present invention.

Referring to FIGS. 1-3, a pump apparatus 10, according to an embodiment of the present disclosure, includes a housing 12 with an inlet 11 to receive working fluid and an outlet 13 to discharge the working fluid. A housing 12 consists of a continuous inner wall that borders an interior chamber 20, within which a rotor 30 with an integrated impeller 32 is mounted. The housing 12 also consists of an outer wall which, with the inner housing wall, forms a space of substantial volume for containing structural components of the magnetic suspension and electric motor. An outlet 13 extends into the housing chamber 20 and communicates with the pump volute 22 that is advantageously constructed for obtaining pressure rise from the kinetic energy of a fluid.

The rotor 30 is disposed for rotation about the central axis z of housing 12, as depicted in FIG. 2. The impeller 32 is composed of a plurality of blades 33 that transfers energy to the working fluid when the impeller 32 rotates. The rotor 30 contains components of the magnetic suspension and electric motor that interact with the corresponding components within the housing 12 to provide the force and torque necessary to suspend and revolve the rotor 30.

According to an embodiment of the present disclosure, the rotor 30 may take an annular shape, and the housing interior chamber 20 may have a corresponding annular channel 24 that accommodates the annular rotor 30. The inner wall of annular channel 24 forms a central post 15 that projects from the bottom surface of annular channel 24. The outer wall of the annular channel 14 attaches to the exterior casing 16 that is a portion of the space between the inner and outer walls of the housing 12. Either the central post 15 or the exterior casing 16, or both, may contain components of the magnetic suspension and/or electric motor.

An xyz coordinate system is represented on the housing 12 as shown in FIGS. 2 through 5. The z axis overlaps with the central axis of the cylindrical surface of central post 15. The xy plane passes through the middle height of the electromagnet pole shoes 83a-d (FIGS. 3, 4, 9(a)).

When the pump 10 is assembled with the rotor 30 placed in the annular channel 24, and the magnetic suspension takes effect properly, the rotor is fully suspended by magnetic forces such that in normal operation no part of the rotor 30 is in physical contact with the housing surface. In this way, the surface of the rotor 30 and the corresponding surface of the annular channel 24 define a U-shaped suspension gap 25 (FIG. 3) therebetween. Also, as the rotor 30 is properly suspended, the passageway of the impeller 32 (with blades 33) becomes aligned with the passageway of the volute 22. Therefore, when the rotor 30 rotates, working fluid entering into the pump 10 through inlet 11 is pushed by the impeller blades 33 to flow radially outwards through the impeller passageway and enters into the volute 22. The fluid is collected by the volute 22 and discharged out of the pump 10 through outlet 13.

Due to pressure differences, a fractional amount of fluid flows through the U-shaped suspension gap 25 and forms a secondary flow around the rotor 30. Since the pressure at the outer opening of the U-shaped suspension gap 25 is greater than the pressure at the inner opening of the "U", the secondary flow is created by fluid entering the outer opening of the gap, flowing downwards on the outer side of the rotor 30, inwards at the bottom of the rotor 30, and upwards on the inner side of the rotor 30, and exiting the U-shaped suspension gap 25 from the inner opening. It can be appreciated that such a secondary flow path, according to an embodiment of the present invention, is straightforward and free from obstructive object or structure, such as zigzag structure, that would otherwise cause flow stagnation or significantly hinder the flow. Consequently, the secondary flow produces unimpeded wash out on the entire rotor surface, which helps to prevent blood clotting, among other benefits in handling stress-sensitive fluids.

According to an embodiment of the present invention, a thin-walled jacket of any suitable material that is compatible with the fluid the pump handles, such as a titanium alloy, or suitable coating may be applied on the rotor surface and the housing inner surface to keep the parts within the rotor 30 and the housing 12 from direct contact with the working fluid. However, for the sake of clarity, such a jacket or coating is not shown in the drawings herein. Further, when addressing principles of operation of the motor and magnetic suspension, the term "air gap," as used herein, designates the gap between magnetic parts although in actual practice such a gap may be filled with fluid and/or any other nonmagnetic materials, or even a vacuum, rather than air.

Figure 4:
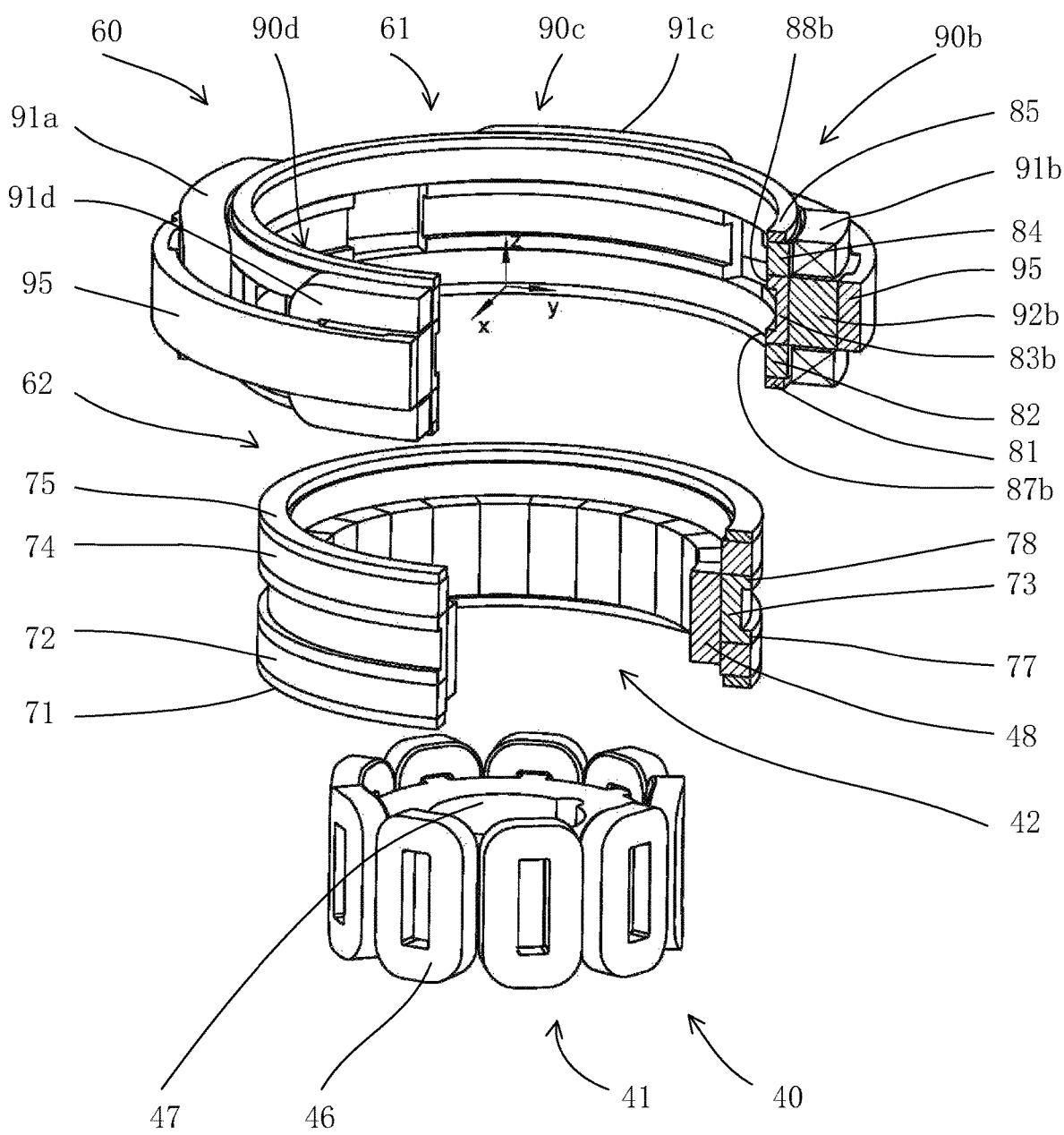
FIG. 4 is an exploded isometric view of the assemblies of the magnetic suspension and the electric motor in the pump of FIG. 1 in accordance with an embodiment the present invention.
Figure 5:
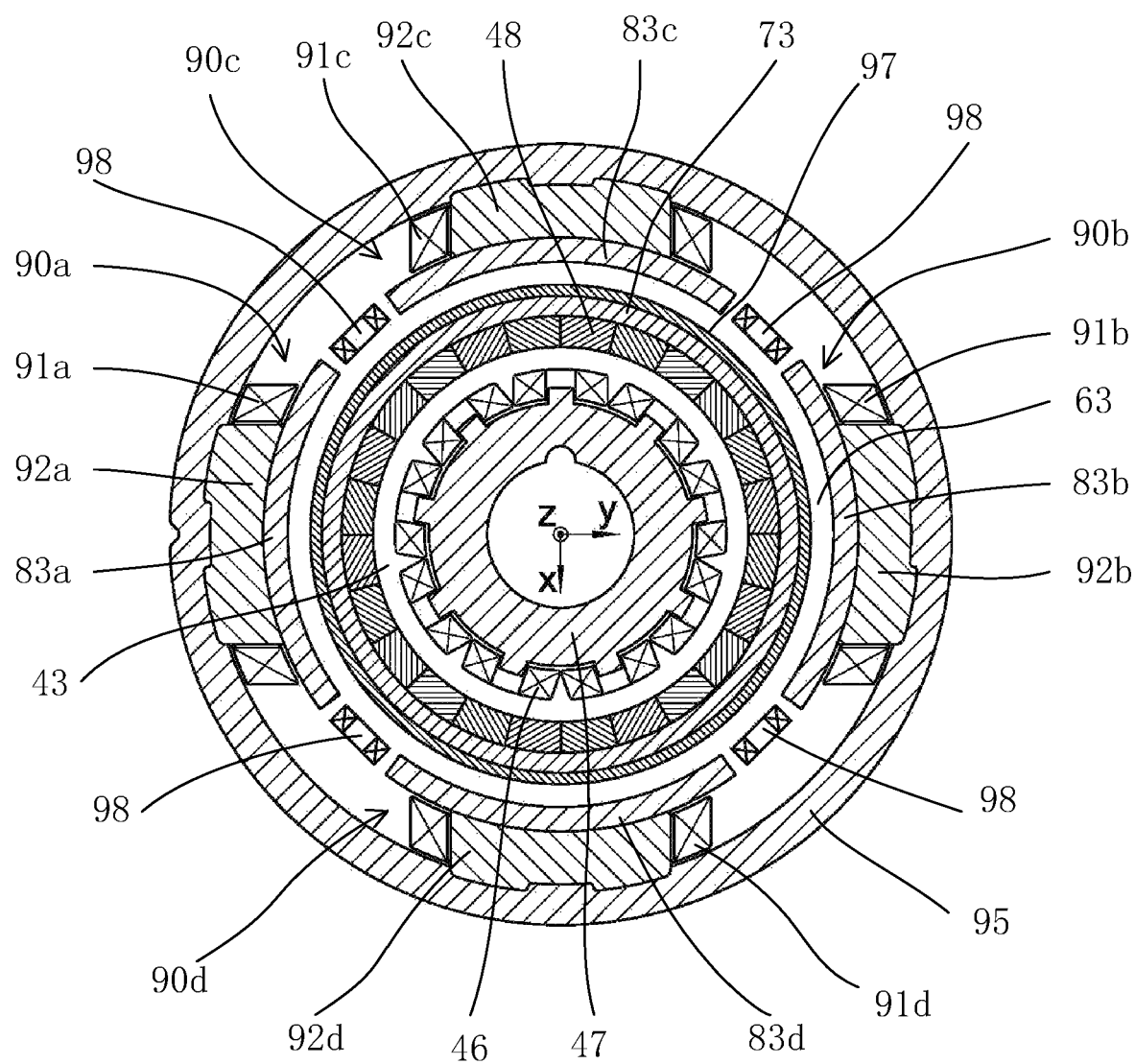
FIG. 5 is a top cross-sectional view of the pump of FIG. 1, in accordance with an embodiment the present invention.

Now turning to FIGS. 3-5, one example embodiment of an electric motor 40 and magnetic suspension 60 is illustrated. The motor 40 is preferably of a brushless DC or brushless AC type, although various other types, such as induction motor, can be employed by one skilled in the art based on the general principles disclosed herein. As is illustrated in FIGS. 3 and 4, a brushless motor 40 consists of a stator assembly 41 mounted within the housing 12 and a rotor assembly 42 mounted within the rotor 30. In this embodiment, the stator assembly 41 is located within the central post 15, but it may alternatively be disposed in another portion of the housing 12, such as exterior casing 16, for example.

The motor stator assembly 41 is disposed closely adjacent to an air gap 43 to favor power efficiency. The motor stator assembly 41 includes a plurality of coils 46 that are grouped into windings of multiple phases, for example 3 phases, as commonly known by those having skill in the field. According to an embodiment of the present disclosure, motor coils 46 are wound around teeth of a motor stator core 47, which is made of a ferromagnetic material, such as soft iron or silicone steel, with a laminated or non-laminated structure. However, the motor stator core 47 may be made in part or entirely of any non-magnetic material in order to reduce or eliminate unbalanced magnetic pull on the rotor 30. The unbalanced magnetic pull is the magnetic force induced between the rotor magnets and the stator magnetic material when the rotor and stator are not in perfect alignment geometrically and magnetically in a radial direction. Such force is generally unwanted, especially in a design with magnetic suspension, since it causes negative stiffness that has to be counterbalanced by magnetic suspension. Therefore, although a motor stator having a ferromagnetic core may contribute to increased power efficiency, such a core structure may not be necessary for optimizing the overall performance of the apparatus, i.e. a coreless motor structure may be used.

The motor rotor assembly 42 includes a plurality of permanent magnet segments 48 installed around the inner periphery of the rotor 30, adjacent to the air gap 43. These permanent magnet segments 48 are mounted piece by piece circumferentially and are configured with alternating polarization to form the magnetic poles of the motor rotor, which generates a circumferentially alternating magnetic field in the air gap 43, as commonly known to one skilled in the art. Preferably, a Halbach array can be employed to form concentrated magnetic field towards air gap 43. Also, a magnetic yoke may be used on the back side of the permanent magnets 48 to advantageously facilitate assembly and enhance magnetic performance. However, it may not be necessary for other considerations, such as reducing the rotor size. According to an embodiment of the present disclosure, the annular pole member or piece 73, a constructional part of the magnetic suspension assembly 60, also serves for the back yoke of permanent motor magnets 48.

Although FIGS. 3-5 show motor 40 located in the inner portion of the pump 10, the motor 40 can be disposed within the outer portion of the pump 10 by inversing its structures inside-out. In that way, the motor stator assembly 41 will be mounted within the exterior casing 16 of the pump housing 12, with the stator core 47, if any, and the winding coils 46 inverted such that the motor coils 46 reside adjacent to the air gap 63. Accordingly, the motor rotor assembly 42 will be moved to the outer periphery of the rotor 30, with permanent magnets 48 and back yoke, if any, inverted inside-out so that magnetic poles are formed in the air gap 63.

In another alternative embodiment, the motor 40 may be disposed within the base portion of the housing 12, beneath the air gap 62 that corresponds to the bottom of the U-shaped gap 25 (FIG. 3). In such a configuration, an axial flux motor similar to that described herein in FIGS. 22 and 23 will be constructed by one skilled in the art in accordance with the principle of the present disclosure.

Turning now to the principle and construction of the magnetic suspension in pump 10, coordinate system xyz, as stated above, is used for referring the five degrees of freedom (DOFs) of the rotor 30 to be stabilized. These five DOFs include one axial displacement along the z axis, two radial displacements along the x and y axis respectively, and two tilting displacements (angular displacement) about the x and y axis respectively. The radial displacements are stabilized through feedback control of an electric current feeding into electromagnetic coils in a hybrid structure of an electromagnet and a permanent magnet. The other DOFs are stabilized by passive suspension, or utilization of permanent magnets.

In accordance with an embodiment of the present disclosure, the passive suspension is comprised of one or several elementary units each including co-axial annular members, respectively, installed in the rotor 30 and stationary casing (within the pump housing 12). The rotor 30 and casing members are separated by a radial air gap, or in other words, they oppose to each other across a radial air gap. Without loss of generality, the concept detailing the outer member on the casing is explained below.

One embodiment of the elementary passive suspension unit is shown in FIG. 6. In this example, both rotor and casing members are advantageously formed into substantially equivalent thickness, although this is not necessary for successful practice of the present invention. In addition, both members 101, 102 are preferably permanent magnets, but any one of them may be replaced with a soft iron part without deviating from the general principle disclosed herein. However, stronger magnetic flux can be produced by using permanent magnets, so that increased suspension stiffness can be obtained in the same amount of space. Using permanent magnets can also reduce negative stiffness in the radial direction, and thus facilitate the radial suspension design for better performance.

As used herein, the term "permanent magnet" or "magnet" refers to a part made of a ferromagnetic material that has a large remanence and a large coercivity, and is magnetized to serve as a source of a magnetic field, such as NeFeB, as commonly known to one skilled in the art. A "soft iron", as used herein refers to a part made of laminated or non-laminated ferromagnetic material that has a small remanence and a small coercivity, and is used for channeling magnetic flux, such as pure iron, silicone steel, or Hiperco alloy, as commonly known to one skilled in the art.

A coordinate system xyz is represented on the stationary casing of FIG. 6. As shown in FIGS. 6(*a*) through 6(*c*), annular members 101, 102, separated by an air-gap 104 are both magnetized along the z axis, but in opposite directions. Letters "N" and "S" denote the north pole and south pole, respectively. Accordingly, these magnets produce a series of loops of working magnetic flux 103 that lie in meridian plan and pass through the interior of both annular members 101, 102, or link these members. Note that the term "working magnetic flux", as used herein stands for the magnetic flux that contributes to the primary forces for suspension, in contrast to the leakage flux.

The passive stability can be appreciated with the principle that a magnetic flux loop tends to minimize its total reluctance. Therefore, annular members 101, 102 tend to align with each other about the center of thickness (along the z axis) as shown in FIG. 6(*a*). If annular member 102 experiences an upward displacement as shown in FIG. 6(*b*), then the net attracting force on the left and right cross-sectional areas of annular member 102 from casing member 101, $f_1$ and $f_2$ respectively, become inclined with respect to the x-y plane. The sum of these forces forms a net force F that pulls annular member 102 downwards, restoring alignment with member 101. This mechanism stabilizes the rotor in axial direction.

As shown in FIG. 6(*c*), if annular member 102 gets an angular displacement (tilting) about the x axis, then distributed attracting forces are induced on annular member 102 from annular member 101. The net force on the right (positive y) cross-sectional area, $f_2$, inclines from the x-y plane towards the negative z direction, while the net force on the left (negative y) cross-sectional area, $f_1$, inclines from the x-y plane towards the positive z direction. If the thicknesses of annular members 101, 102 are sufficiently small relative to the diameter of the air gap 104 and the tilting angle is sufficiently small, then the acting point of force $f_2$ locates above the acting point of force $f_1$. Therefore, a net torque T on annular member 102 occurs thereby tending to realign the rotor member with the casing member. This mechanism provides tilting stability of the rotor with passive suspension.

The suspension described above is inherently unstable in the radial direction. If the annular member 102 becomes misaligned with the casing member 103 in the radial direction of FIG. 6(a), a net attracting force may be induced on annular member 102 to push it further away from the center, increasing the misalignment until the annular member 102 touches the inner surface of the casing member 103. In fact, the passive suspension of embodiments of the present invention is characterized by distributed attracting forces in a radial direction between the rotor and casing members, rather than repulsive forces in the radial direction or attracting forces in an axial direction. If otherwise two concentric annular members 111, 112 are magnetized in the same direction as illustrated in FIG. 7, then a distributed repulsive force is brought about between annular members 111, 112 in radial direction. As such, the working magnetic flux of any of the annular members 111, 112 of FIG. 7 completes a loop (e.g. flex loop 114) that merely passes through the interior of that magnet member itself (annular member 112), but not through the other member (annular member 111). A similar effect may occur with other respective annular members (e.g. flux loop 113). In other words, the magnetic flux does not link the rotor and casing members that oppose to each other across a radial air gap 115. Such a configuration does not serve for passive suspension of this invention.

Therefore, in accordance with an embodiment of the present invention, passive suspension is achieved with working magnetic flux loop that links rotor and casing members that oppose to each other across a radial air gap. As long as the overall thickness of the suspension unit is sufficiently small in comparison with the diameter of the air gap, passive stability in axial displacement and tilting displacement can be obtained. This principle is referred to as the principle of flux loop linkage and is the sufficient criteria for achieving passive suspension in this disclosure. For example, a valid suspension remains if one of the members 101, 102 of FIGS. 6(a)-(c) is replaced with a soft iron, since the flux loop still passes through the interior of the both members.

Figure 6A:
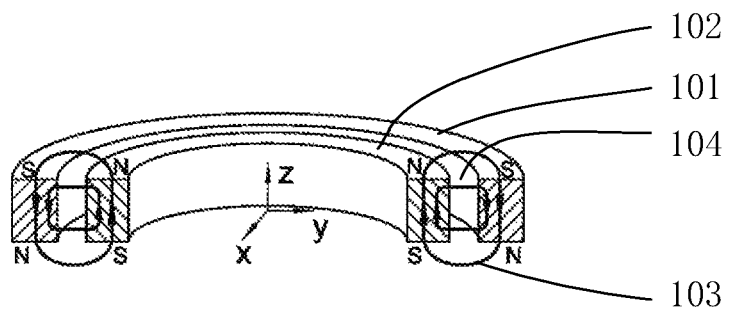
FIGS. 6(a), 6(b), 6(c), and 6(d) depict an elementary passive suspension unit consisting of magnetically coupled annular members in the rotor and the casing respectively, in accordance with an embodiment the present invention.
Figure 6D:
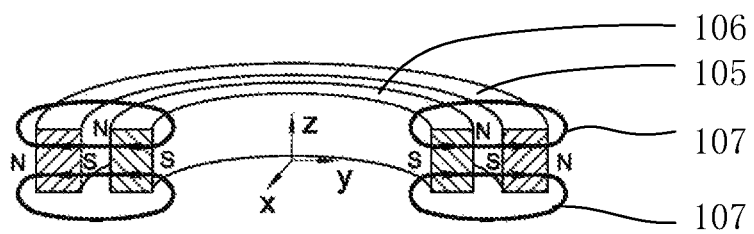
Figure 7:
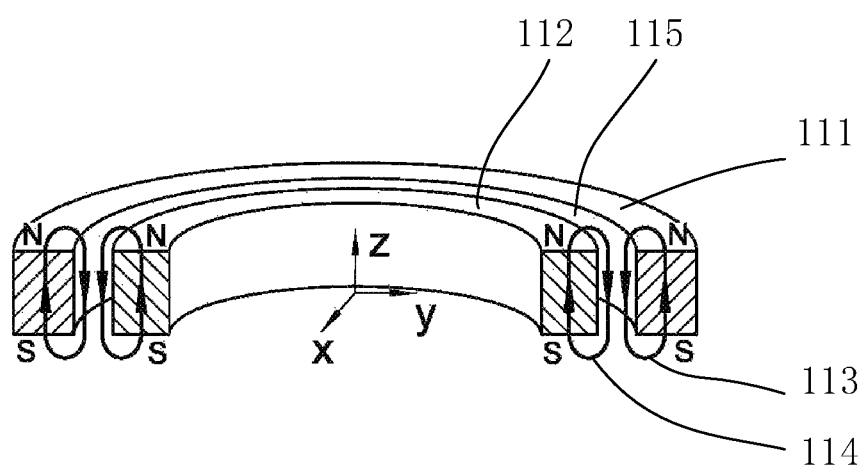
FIG. 7 depicts elementary passive suspension units in which a magnetic flux does not link the rotor and casing members.

Although the magnets of FIG. 6(a) are axially polarized, various other arrangements may be employed by one skilled in the art to create the same effect of passive suspension based on the principles disclosed herein. For example, as shown in FIG. 6(d), the annular member magnets 105, 106 are polarized in a radial direction, which creates a working flux loop 107 that links the magnets 105, 106. This construction can serve substantially the same function of passive suspension for axial displacement and tilting. Other combinations of polarization of magnets, e.g. one axially polarized and the other radially polarized, may also be used. Such operable examples also include magnets polarized in an inclined direction with respect to the z axis.

Figure 6B:
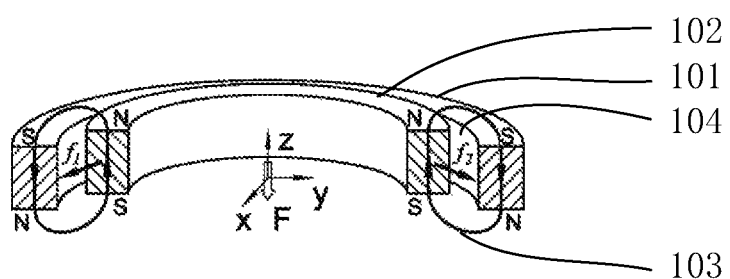
Figure 6C:
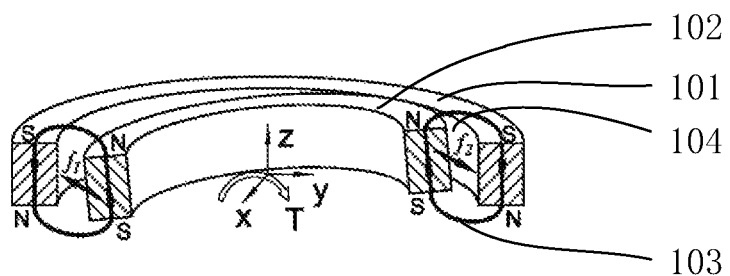

The elementary suspension unit described above can be enhanced by adding annular plates of soft iron onto one or both ends of any axially magnetized permanent magnet of FIGS. 6(a)-(c). Such a plate, namely end pole piece, serves to concentrate magnetic flux into the soft iron and brings about intensified magnetic flux density in the air gap. A magnetic force applied on a surface of highly permeable magnetic material depends not only on the total flux over the surface, but also on the flux density on the surface. For the same total flux going into or out of a surface, the higher the flux density on the surface is, the greater the magnetic force the surface experiences. Therefore, by adding end pole pieces on the ends of the permanent magnets in an elementary suspension unit of FIGS. 6(a)-(c), increased suspension stiffness can be obtained with same volume of permanent magnet.

The annular members of permanent magnet or soft iron in the rotor of a magnetic suspension assembly of the embodiments of the present invention are preferably complete rings substantially uniform in geometry and magnetic characteristics around the circumference. An otherwise discontinuous structure that produces a significantly varying magnetic field around the circumference of rotor can bring about undesirable effects when the rotor rotates. For example, the variation of the magnetic field may lead to an unsteady suspension force and stiffness as the rotor rotates, which can cause vibration and other undesirable dynamic effects. It also induces an eddy current in electrically conducting materials in the casing, which can cause energy loss and heating.

Adversely, some or all of the annular members in the casing of a magnetic suspension assembly of the embodiments of the present invention may be formed of geometrically or magnetically non-uniform or interrupted structures. This is because such an alternative structure by itself does not cause a variation of suspension force or an eddy current as the rotor rotates. For example, a set of arcuated segments of permanent magnets or soft iron evenly distributed along a circle, especially if the segments together cover the majority of the circle, can suitably serve for the magnetic suspension of the embodiments of the present invention.

Figure 8:
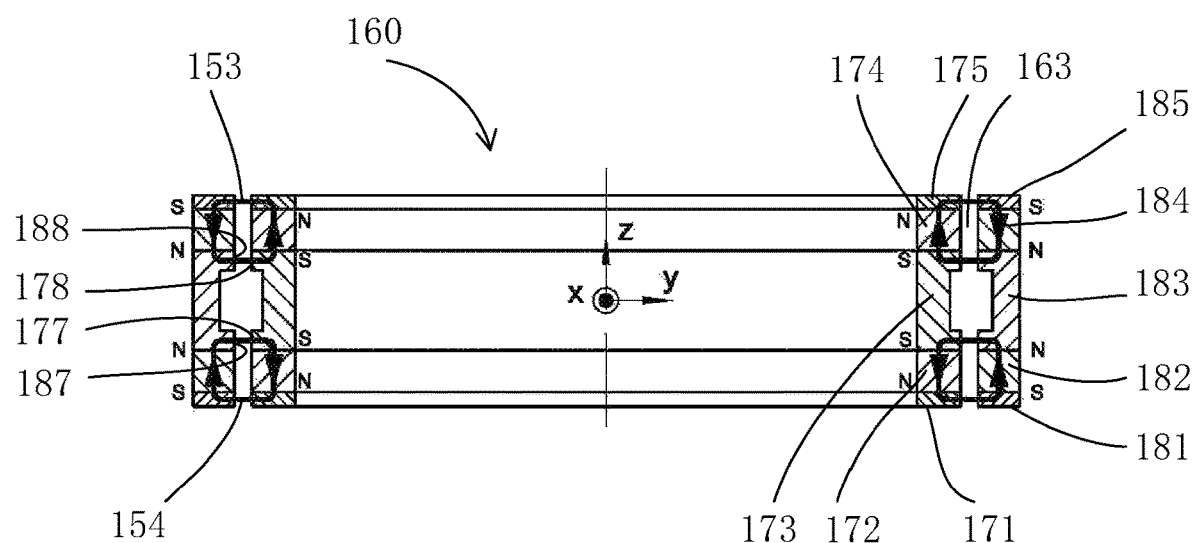
FIG. 8 is a front cross-sectional view of an exemplary passive suspension unit in accordance with an embodiment the present invention.

The elementary passive suspension unit, discussed above, may be used as an independent structure, or by forming a stack of multiple units in an arrangement of alternating magnetic polarizations between neighboring units. FIG. 8 illustrates an embodiment of such a stacked structure in accordance with this principle. As discussed above, tilt stability of an elementary passive suspension unit, such as that of FIGS. 6(a)-(d), requires sufficiently small thickness of annular magnetic members in comparison with the diameter of the air gap. According to the same principle, in order to achieve tilt stability of a stacked structure, the overall thickness of the stack is made sufficiently small relative to the diameter of the air gap.

As shown in FIG. 8, the passive suspension assembly 160 consists of symmetrical upper and lower portions. The upper portion includes an annular permanent magnet 184 disposed within the casing and an annular permanent magnet 174 within the rotor. These magnets are preferably of substantially equivalent thickness and face to each other across a radial air gap 163. An annular end pole piece 185 of soft iron is attached to the top end of the magnet 184. This end pole piece 185 may or may not project from the inner cylindrical surface of the magnet 184 towards air gap 163, depending on an analysis of design optimization. Correspondingly, an annular end pole piece 175 of soft iron is attached to the top end of the magnet 174, and it may or may not project from the outer cylindrical surface of the magnet 174 towards the air gap 163. The end pole pieces 175, 185 are preferably of substantially equivalent thickness and oppose to each other across air gap 163. In addition, a pole member 183 of annular soft iron is attached to the bottom end of magnet 184. Pole member 183 may advantageously have an annular groove cut on the inner cylindrical surface to form a tooth 188 and a tooth 187 on the upper and lower ends of the pole member 183 respectively, both projecting towards the air gap 163. Correspondingly, another pole member or piece 173 of annular soft iron is attached to the bottom end of the magnet 174, and it may have an annular groove cut on the outer cylindrical surface to form teeth 178, 177 that project towards the air gap 163. The pole members 183, 173 are preferably of substantially equivalent thickness, as well is the thickness of each couple of teeth 188, 178, 187, 177, consistent with the same feature of the coupled end pole pieces 185, 175.

The annular permanent magnets 184, 174 are both magnetized across thickness (along axis z) but in opposite directions. The soft iron members sandwiching these magnets serve to channel the magnetic flux through the magnetic materials and air gap. Therefore, annular permanent magnet 184, 174 generate a group of magnetic flux loops 153, which passes through the annular permanent magnet 174, the end pole piece 175, the air gap 163, the end pole piece 185, the annular permanent magnet 184, the pole member 183, the air gap 163, and the pole member 173. A group of rotor members 173, 174, 175, and a group of casing members 185, 184, 183 are thus linked by the working magnetic flux loop 153.

The structure in the lower portion of assembly 160 can be formed by mirroring the upper structure about the x-y plane that extends through the middle of thickness of the pole members 183, 173. Accordingly, coupled members of magnets 182, 172, end pole pieces 181, 171, teeth 187, 177 are formed. A flux loop 154 links the magnetic members in the rotor with the magnetic members in the casing. The magnets sandwiching the pole members 183, 173 are magnetized in opposite directions such that the working magnetic flux loops 153 and 154 circle in opposite directions.

Therefore, the rotor members and casing members of the stacked structure 160 is linked by a group of magnetic flux loops 153, 154. In addition, the overall thickness of the assembly 160 is made sufficiently small relative to the diameter of the air gap 163. Therefore, according to the above stated principle of flux loop linkage, the assembly 160 characterized by the magnetic flux loops 153, 154 can serve for passive suspension for axial and tilting stability.

The pole members 183, 173 play the same role of focusing magnetic flux into a confined air gap area as do the end pole pieces 185, 175. The teeth 188, 178, 187, 177 in these pole members may contribute to further focusing the magnetic flux into an even narrower air gap in between the opposing teeth compared to the air gap in between the entire pole members. However, part or all of the tooth structures are not necessary in some applications depending on design optimization, which means any or both of the grooves on the pole members 183, 173 may not be needed.

It should be noted that the components of FIG. 8 may or may not be a continuous annular piece along circumference. For example, any member such as the casing pole piece 183 can be replaced with a plurality of arcuated segments disposed in the original space of the annular piece 183. This alteration does not deviate from the principle of magnetic suspension disclosed herein, although certain suspension performances may be affected. Specifically, if a rotor member is made with an interrupted structure, an unsteady suspension force and an eddy current may be induced when the rotor spins, which may impair power efficiency, dynamic performance and possibly other performances.

The pole members 183, 173 can be made the same as the end pole pieces 185, 175 if the assembly 160 is employed merely for passive suspension. However, the construction with thicker pole members 183, 173 can be adapted to form a hybrid magnetic suspension of FIGS. 3-5 that serves an additional function of active suspension for radial stability. Returning to FIGS. 3-5, the suspension assembly 60 may have nearly the same construction as the assembly 160 of FIG. 8. In fact, the reference numerals of each component of FIG. 8 corresponds to those of FIGS. 3-5, albeit with a trailing 0 (i.e. changing 160 to 60). Each reference numeral of FIG. 8 (with a trailing 0) can find a similar numeral in FIG. 3 with the associated structural members matching with each other, except for the pole member 183. The pole member 183 of FIG. 8 is replaced by a plurality of electromagnet pole shoes 83a-d (FIG. 5) distributed circumferentially around the air gap 63 in order to serve for the electromagnet functions to be discussed below. This group of pole shoes can be viewed as being made by cutting off some sections along the circumference of the continuous annular pole member 183. Such replacement of a continuous ring with interrupted annular segments does not change the principle of passive suspension, and will not cause significant change in suspension performance since a majority of circumferential space is still occupied by soft iron. Therefore, the passive suspension assembly in the pump 10, in accordance with an embodiment of the present invention, is constructed with the above examples.

Turning now to the principle and construction of the active suspension in pump 10 of FIG. 1. the active suspension is based on a principle of magnetic flux modulation on bias flux. The bias magnetic flux is established by permanent magnets, and the modulating magnetic flux is generated by electromagnets.

Referring to FIGS. 3-5, a magnetic suspension assembly 60 includes a rotor assembly 62 and a casing assembly 61 separated by an air gap 63. The rotor assembly 62 includes, among others, a primary pole piece 73 sandwiched by permanent magnets 72, 74 possessing opposite polarizations. The casing assembly 61 includes, among others, a group of pole pieces 83a-83d that are sandwiched by permanent magnets 82, 84 possessing opposite polarizations. In addition, the casing assembly 61 consists of a group of electromagnet units 90a-d evenly distributed around the periphery of the casing assembly 61. Each electromagnet unit has substantially the same construction. Therefore, for simplicity, they are described with a representative unit subtracting the alphabetic suffix from the numeral. For example, unit 90 is a representative of any of the four units 90a-d. This convention is used throughout this document.

Thus, an electromagnet unit 90 is comprised primarily of a coil 91, an iron core 92, a pole shoe 83, and a back yoke 95 that is shared by a set of electromagnet units. The iron core 92 is a cubic piece made of soft iron with a cross sectional shape such as circular, rectangular with rounded corners, or others that are known to one skilled in the art to be suitable for construction of electromagnet core. The iron core 92 is advantageously mounted into the assembly 61 by aligning its longitudinal axis in a radial direction, like a spoke of a wheel. A coil 91 for conducting electric current is wound around the iron core 92. A pole shoe 83 is attached to one end of the iron core 92 on the side towards the air gap 63. A back yoke 95 is attached to the other end of iron core 92.

The pole shoes 83a-83d are evenly distributed circumferentially around the air gap 63. Each pole shoe serves for coupling with the rotor primary pole piece 73 to form concentrated magnetic flux through the air gap. Accordingly, teeth 88, 87 are constructed on the inner surface of the pole shoe 83 to oppose the teeth 78, 77 of the primary pole piece 73 respectively, if the latter teeth are present. For optimal design of active suspension, the circumferential gap between the neighboring pole shoes is determined to minimize flux leakage in between the pole shoes while maximizing the inner surface of each pole shoe for best conducting working flux through the air gap. An annular end pole piece 85 of soft iron is attached to the top end of the magnet 84. This end pole piece 85 may or may not project from the inner cylindrical surface of the magnet 84 towards air gap 63, depending on an analysis of design optimization. Correspondingly, an annular end pole piece 75 of soft iron is attached to the top end of the magnet 74, and it may or may not project from the outer cylindrical surface of the magnet 74 towards the air gap 63. The end pole pieces 75, 85 are preferably of substantially equivalent thickness and oppose to each other across air gap 63.

Referring to FIGS. 3-5, in accordance with an embodiment of the present disclosure, a back yoke 95 is configured to connect the electromagnet units that jointly serve for control of one DOF. Particularly, the electromagnet units 90a, 90b are connected by back yoke 95 to jointly control the rotor's radial position along the y axis, and electromagnetic units 90c, 90d are connected to control the rotor along the x axis. In FIGS. 3-5, one back yoke 95 connects all electromagnet units, which is beneficial for simplicity and compactness, among other advantages. However, in some applications, coupling between magnetic flux from different sets of electromagnet units is to be strictly limited to suppress interference between the x axis control and y axis control. In that case, separate back yokes may be configured so that each back yoke only connects those electromagnetic units that merely work for controlling one particular radial displacement (along the x or y axis). Such an alternative construction can be readily conceived by one skilled in the art in light of the principle disclosed herein.

Active control of the rotor's radial position is achieved through real time adjustment of magnetic force on the rotor from the casing, mainly the magnetic force on the primary pole piece 73 from the electromagnet pole shoes 83a-83d. In the embodiment of FIGS. 3-5, radial displacement in the x or y direction is independently controlled, with two electromagnets 90a, 90b responsible for the y axis control, and two electromagnets 90c, 90d for the x axis control. Since the basic principle of control on each of the axes is the same, only the y axis control is to be discussed in detail below. The active suspension in the embodiments of the present invention is based on a mechanism called push-pull modulation of the bias magnetic flux in air gap. As illustrated in the upper portion of the symmetrical structure of FIG. 9(a), permanent magnets 84, 74 generate a group of magnetic flux loops 53a-53d that pass through the air gap 51a-51d between the rotor primary pole piece 73 and the electromagnet pole shoes 83a-83d respectively. Such working magnetic flux in the air gap for suspension is referred to as bias flux. A length of flux loops 53a, 53b can be seen in FIG. 9(b) which is a cross sectional view of FIG. 9(a) with cutting plane A-A passing through the air gap 51a, 51b. A dot inside a circle indicates flux going out of the page, and an "x" inside a circle indicates flux going into the page. The teeth on the pole members 73, 83 have an effect of focusing the bias flux in the confined areas in the air gap 51. In a same manner, another set of bias magnetic flux loops 54a, 54b is established in the lower portion of the symmetrical structure of FIG. 9(a). Since both sets of bias magnetic flux are substantially symmetrical and produce active control forces with the same mechanism, only active control with flux loops 53a, 53b is to be further discussed below. Note that the total active control force on the rotor is a sum of forces from these two sources.

A magnetic force on a tooth 78 of the rotor from the tooth 88a of the casing pulls the rotor in a negative y direction, and a magnetic force from the tooth 88b of the casing pulls the rotor in a positive y direction. Since the magnetic suspension assembly 60 of FIGS. 9(a) and (b) has a symmetrical construction about the x-z plan, when the rotor is set concentrically with the casing, bias flux in the air gap 51a, 51b are substantially identical in magnitude. Therefore, magnetic forces due to bias flux in the air gaps 51a, 51b substantially counterbalance each other, resulting in a practically zero net force.

Figure 9A:
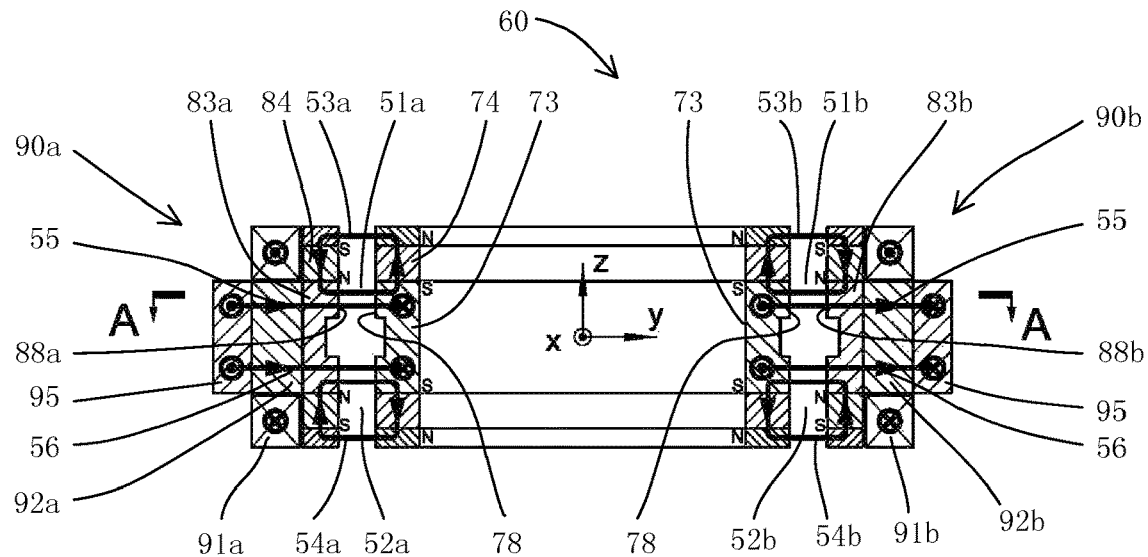
FIGS. 9(a), 9(b) are cross-sectional views of the magnetic suspension assembly in the pump of FIGS. 3 through 5.
Figure 9B:
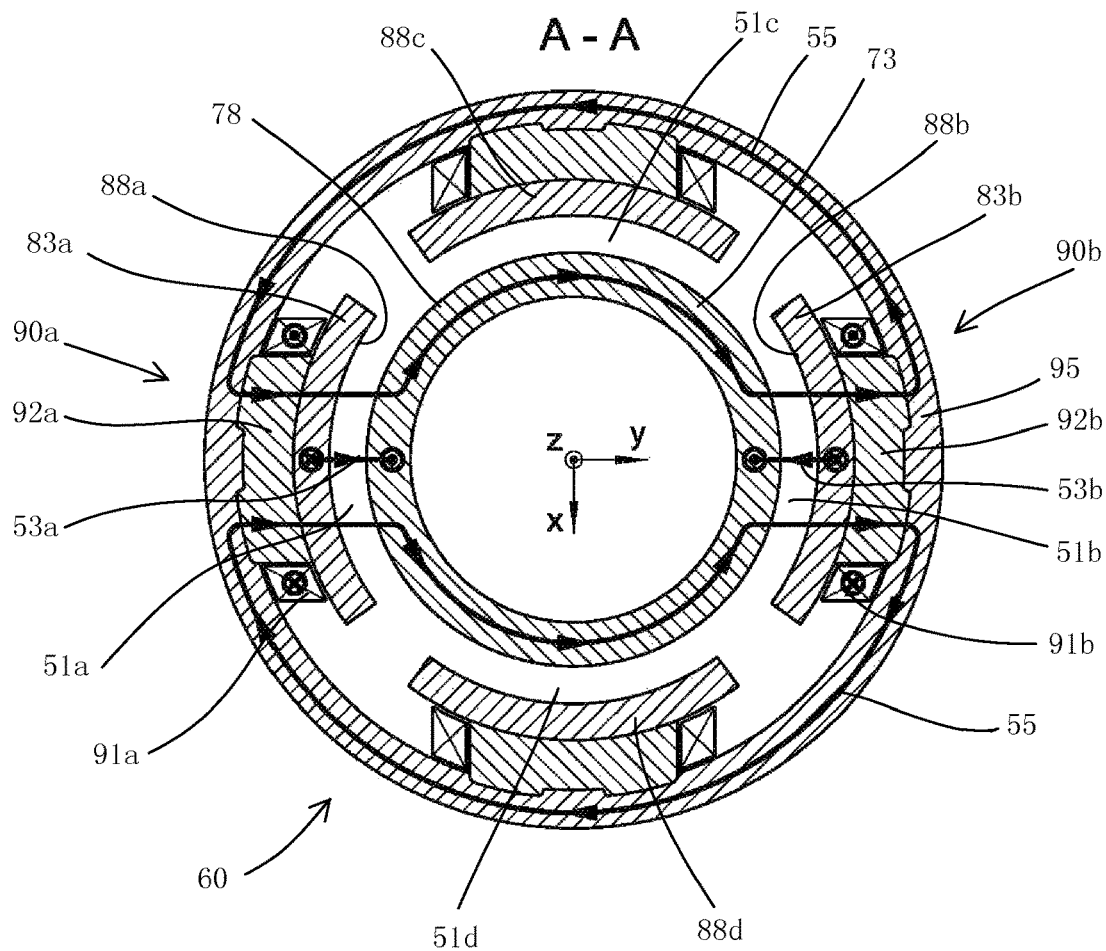

Suppose electric current, i, is fed into the coils 91a, 91b in directions as shown in FIGS. 9(a) and (b), where a dot inside a circle symbolizes current flowing out of the page, and an "x" inside a circle symbolizes current flowing into the page. The coils 91a, 91b are connected in series so that they work jointly with same current to produce substantially the same amount of magnetic flux in the iron cores 92a, 92b respectively. Such working magnetic flux for suspension generated by electromagnets is referred to herein as modulating flux. As shown in FIG. 9, since the overall suspension assembly 60 is symmetrical about the y-z plan and x-y plan, the modulating flux produced by electromagnets 90a, 90b makes either the modulating flux loop 55 in the upper portion of the assembly 60, or the modulating flux loop 56 in the lower portion of the assembly 60. The flux loops 55, 56 are substantially identical for the same reason as with the above bias flux loops 53, 54, and so only the modulating flux loop 55 is analyzed below. The modulating flux loop 55 passes through the electromagnet iron core 92a, teeth 88a of the pole shoe 83a, the air gap 51a, and enters the teeth 78 of the rotor primary pole piece 73 on the negative y side. It then passes along the periphery of the rotor primary pole piece 73 to the positive y side, exiting the teeth 78, passing through the air gap 51b, the tooth 88b of the pole shoe 83b, the iron core 92b, and entering the back yoke 95, and finally passes along the periphery of the back yoke 95 to the negative y side to complete the loop. Since the magnetic flux passing through the iron cores 92a, 92b are substantially identical in magnitude, flux going into the other iron core through the air gap 51c, 51d in x direction, i.e. the flux leakage, is negligible.

The modulating flux 55 superimposes the bias flux 53a, 53b in the air gap 51a, 51b. With the particular directions of the magnetic flux loops indicated in FIGS. 9(a) and (b), but without loss of generality, the modulating flux 55 goes in the same direction with the bias flux 53a in air gap 51a, but in opposite direction to the bias flux 53b in the air gap 51b. Therefore, the magnetic flux in the air gap 51a is enhanced above the bias flux, and thus the magnetic force between the pole shoe tooth 88a and the rotor pole piece tooth 78 is increased. Meanwhile, the magnetic flux in the air gap 51b is reduced from the bias flux, and thus the magnetic force between the pole shoe tooth 88b and the rotor pole piece tooth 78 is decreased. These effects combine in a push-and-pull manner so that a net magnetic force on the rotor towards the negative y direction results. If the electric current increases, then the resultant force on the rotor increases in magnitude. Also, if the electric current reverses, then the resultant magnetic force changes to the opposite direction. The mechanism of imposing paired, opposite modulating flux on bias flux in the air gap to create controllable net magnetic force, the so-called push-pull modulation, is thus demonstrated.

Suppose the air gap flux density of the bias flux and the modulating flux is B and ΔB, respectively. The flux density in the air gap 51*a*, 51*b* becomes B+ΔB and B−ΔB respectively. According to magnetics theory, the magnetic force on a surface of highly permeable magnetic material is in approximate proportion to the product of the square of flux density on the surface and the surface area. Therefore, the above analysis yields the following net magnetic force $$F = k \cdot S \cdot [-(B+\Delta B)^2 + (B-\Delta B)^2] = -4k \cdot S \cdot B \cdot \Delta B \quad (1)$$

where S is the surface area of the inner surface of tooth 88 (88*a*, 88*b*) of the electromagnet pole shoe, and k is a constant.

Further, the air gap flux density generated by the electromagnet unit, ΔB, is in proportion to electric current in the electromagnet, i, as long as the corresponding magnetic circuit is not saturated. Therefore, Equation (1) can be rewritten as $$F = c \cdot B \cdot i \quad (2)$$

where c is a constant.

The air gap flux density, B, generated by the permanent magnet does not vary with electric current i. Therefore, Equation (2) shows that the net magnetic force is in direct proportion to the electromagnet current. That is, there is a linear relationship between the active control force and the control current. This attribute of the push-pull modulation is advantageous, since, among other advantages, it allows application of linear control strategy for achieving preferred active control performances.

It can be appreciated that according to embodiments of the present invention, the bias flux loop and the modulating flux loop take different pathways in a three dimensional configuration so that they only overlap in the vicinity of the air gap for active suspension control. In a non-limiting example, as shown in FIGS. 9(*a*) and (*b*), the bias flux loops 53*a*, 53*b*, 54*a*, 54*b* lie in meridian plans and modulating flux loop 55, 56 lie in planes parallel to the equator plan. They overlap merely in the air gap 51 and neighboring pole pieces including the rotor primary pole piece 73 and the electromagnet pole shoe 83. In general, in accordance with an embodiment of the present disclosure, the bias flux loops 53*a*, 53*b*, 54*a*, 54*b* do not pass through the iron core of electromagnet, and the modulating flux loop 55, 56 does not pass through the permanent magnet. This aspect of the present invention advantageously differs from the conventional designs such as those described in U.S. Pat. Nos. 8,288,906 and 8,596,999. The permanent magnet has extremely low magnetic permeability to external magnetic flux (close to vacuum) and thus exhibits high reluctance in a magnetic circuit energized by an electromagnet. Therefore, any configuration with the working magnet flux loop of electromagnet passing through permanent magnet will hamper power efficiency or cause significant increase of the coil size. On the other hand, if the working magnetic flux generated by the permanent magnet is configured to pass through the iron core of the electromagnet, then the cross-sectional area of the iron core must be enlarged to avoid saturation. In comparison with a modulating flux, the bias flux must be greater, often significantly, in magnitude in order to cover the entire variation range of modulating flux during operation. Therefore, the increase in the size of electromagnet due to involving its iron core in a permanent magnet circuit can be significant, and thus should be avoided.

Figure 10:
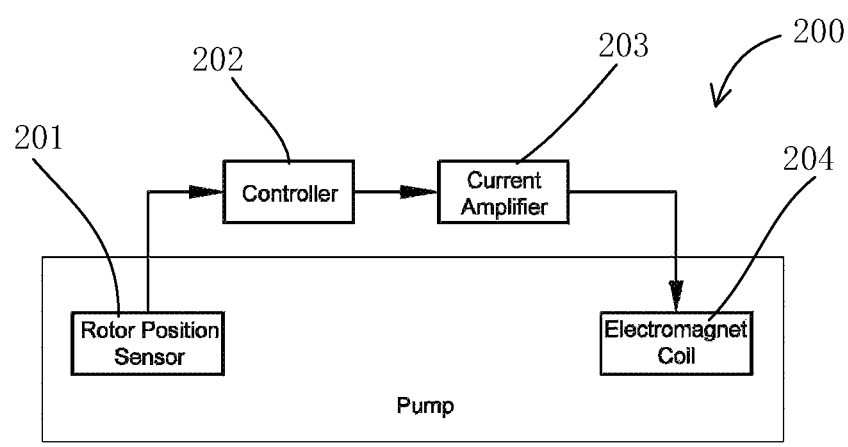
FIG. 10 is a schematic drawing of the feedback control loop for active suspension control in accordance with an embodiment of the present invention.

Active suspension for the radial displacements along the x and y axes is achieved with a feedback control system based on the principle of bias flux modulation disclosed herein. In one embodiment of the present invention, the displacement along x or y axis is independently controlled, so two substantially identical control systems can be employed. As schematically shown in FIG. 10, such a control system 200 includes a position sensor 201 to detect the real time displacement of the rotor along x or y axis. A controller 202 processes the displacement signal coming from the sensor 201 with an appropriate control strategy, and yields commands of control. Various control strategies, such as the proportional differentiation (PD) control, commonly known to those having skills in the magnetic suspension field can be adopted. The control commands are fed into a current amplifier 203 to produce a time-varying electric current with sufficient power capability for actuating the electromagnets. This current flows into the coils of the electromagnet 204 to create the modulating magnetic flux and thus fulfills the goal of active suspension control. The rotor position sensor 201 can be any suitable type for noncontact measurement of the rotor's position, such as an eddy current displacement sensor or Hall effect sensor that is commonly known to one skilled in the field of magnetic suspension. For example, FIG. 5 shows a number of eddy current sensor probes 98, constructed with coils for working with high frequency excitation current, distributed in the gap between electromagnet pole shoes 83*a*-83*d* right-adjacent to air gap 63. Correspondingly, an annular piece 97 made of an electric conductor such as copper is installed in the outer surface groove of the rotor, in FIGS. 3 and 5, right adjacent to the air gap 63 and directly facing the eddy current probe 98, to serve as the target of the eddy current sensor probe 98. The rotor's radial displacements along the axes pointing to the sensor probes 98 are transformed to yield displacements along the x and y axes. Two or more sensor probes 98 are used to obtain the necessary displacement signals.

It can be appreciated that according to embodiments of the present invention, the bias flux not only constitutes the basis of active suspension, but also by itself can serve for passive suspension. This is because a bias flux loop links members in the rotor and the casing that oppose each other across a radial air gap. According to the principle of magnetic flux linkage discussed above for FIG. 6, such a flux loop can serve the function of passive suspension for axial and tilting stability. Therefore, the hybrid magnetic suspension construction of FIGS. 9(*a*) and (*b*) can be advantageously simplified by including fewer members that serve for passive suspension. In general, an elementary hybrid suspension unit according to an aspect of this disclosure may merely include generation of bias magnetic flux and modulating magnetic flux in an air gap that is defined by an annular rotor primary pole piece and a plurality of circumferentially distributed pole shoes of electromagnet units. Various alternative embodiments can thusly be conceived. A few such examples are shown in FIG. 11.

Figure 11A:
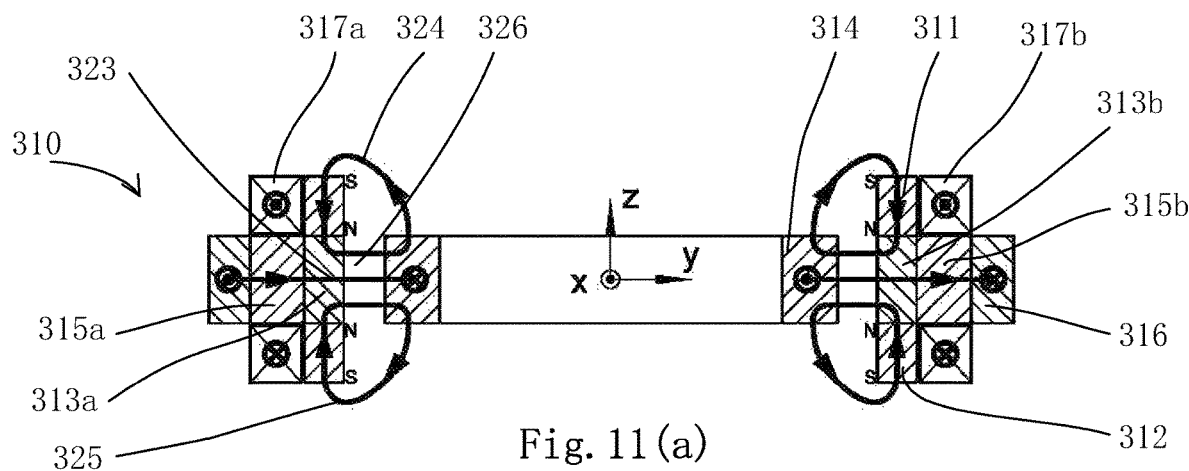
FIGS. 11(a), 11(b), 11(c) are cross-sectional views of various elementary magnetic suspension units that can be employed in a pump in accordance with an embodiment of the present invention.

FIG. 11(*a*) shows an exemplary hybrid magnetic suspension assembly 310 that is simplified from FIGS. 9(*a*) and (*b*) and still holds the fundamental function of full magnetic suspension in accordance with embodiments of the present invention. The rotor assembly is extensively simplified into a single piece of annular soft iron 314, which serves the same function of the rotor primary pole piece 73 of FIGS. 9(*a*) and (*b*). The casing assembly is constructed according to the same fundamental concept of FIGS. 9(*a*) and (*b*) with end pole pieces on the ends of permanent magnets being omitted for constructional simplicity. A number of electromagnets are distributed around the air gap 326, each including a pole shoe 313*a*, 313*b*, an iron core 315*a*, 315*b*, a coil 317a, 317b, and a back yoke 316. The cross-sectional view of FIG. 11(a) depicts two electromagnets, however it will be appreciated that in the embodiment described, additional electromagnets may be contemplated, however, due to the cross sectional view are not shown. The annular permanent magnets 311 and 312, which are preferably continuous rings, sandwich the pole shoes 313a, 313b with opposing magnetic polarizations. Two substantially symmetric bias flux loops 324, 325 are thus generated on both ends of the pole shoes 313a, 313b. These flux loops link the rotor member 314 with a group of casing members 311, 313a, 313b, and 312.

Figure 11B:
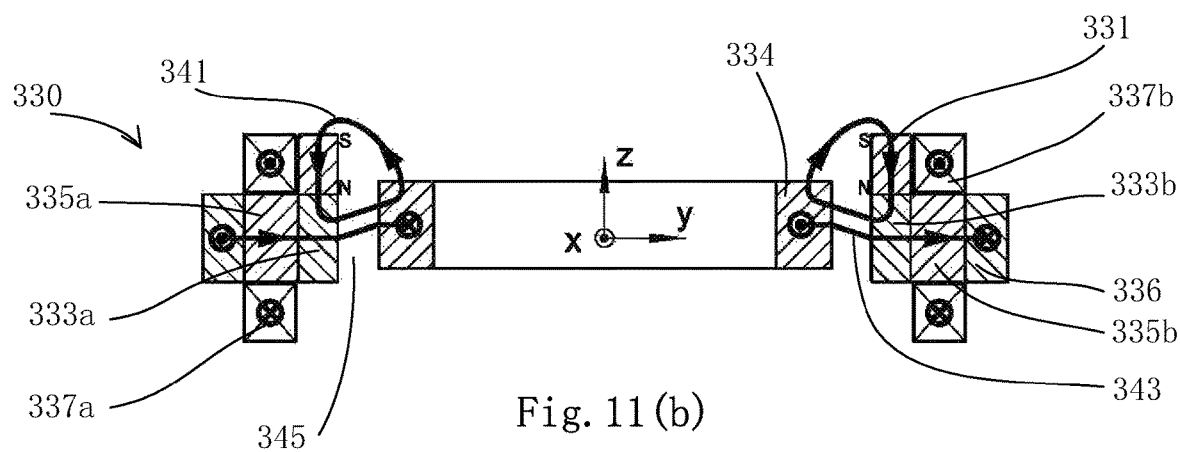

FIG. 11(b) shows an elementary hybrid suspension unit that is further simplified from FIG. 11(a) by including one permanent magnet 331 in the casing. This magnet generates a bias flux 341 that links the rotor primary pole piece 334 with casing members including the permanent magnet 331 and the electromagnet pole shoe 333a, 333b. A number of electromagnets are distributed around the air gap 343, each including a pole shoe 337a, 337b, an iron core 335a, 335b, a coil 337a, 337b, and a back yoke 336. The cross-sectional view of FIG. 11(b) depicts two electromagnets, however it will be appreciated that in the embodiment described, additional electromagnets may be contemplated, however, due to the cross sectional view are not shown. The configuration of FIG. 11(b) fulfills the fundamental function of magnetic suspension in this invention, although many additional suspension performances, such as compactness, dynamics, and power efficiency, may be different. Since the casing of FIG. 11(b) is not symmetrical about the x-y plan, with the passive suspension in the axial direction, the rotor primary pole piece 334 will find an equilibrium position by offsetting a distance from aligning with the pole shoe 333 towards the permanent magnet 331. Accordingly, the modulating flux line 343 in the air gap 345 is tilted with respect to the x-y plane, as well as the active control force that points along flux line 343. The active control force thus gets an axial component that pulls the rotor primary pole piece 334 axially towards pole shoe 333a, 333b. This axial force can be counterbalanced by the passive suspension if a proper design is adapted. However, during operation of the pump, the active control force is adjusted in real time to maintain suspension stability. So, the active control will induce a time-varying axial force on the rotor, which is an internal disturbance on the passive suspension. This disturbance may stimulate axial vibration or even resonance of rotor, among other undesirable dynamic issues, since the passive suspension does not possess an active mechanism to adequately damp the vibration. Therefore, the asymmetric construction of FIG. 11(b) may be less preferable than a symmetric one such as that of FIG. 11(a) in terms of disturbance of active control on passive suspension.

Figure 11C:
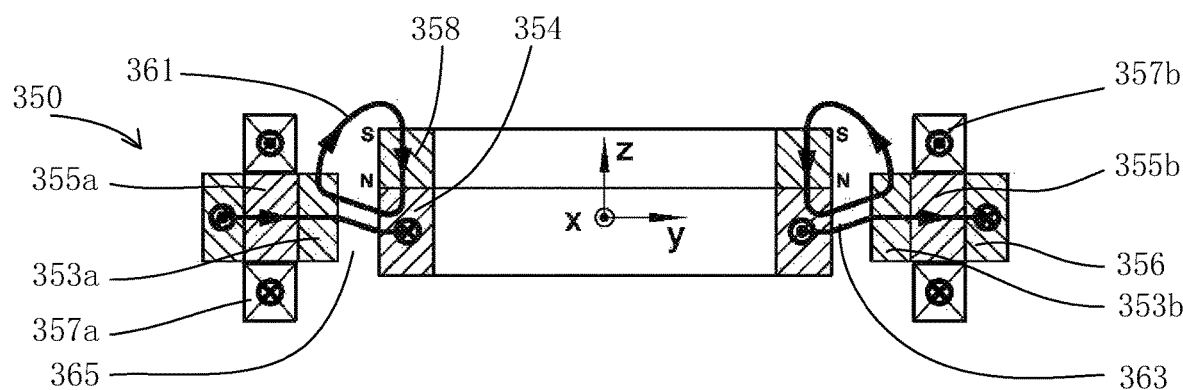

FIG. 11(c) shows another elementary hybrid magnetic suspension unit that is constructed by moving the permanent magnet of FIG. 11(b) from the casing to the rotor. A number of electromagnets are distributed around the air gap 365, each including a pole shoe 353a, 353b, an iron core 355a, 355b, a coil 357a, 357b, and a back yoke 356. The cross-sectional view of FIG. 11(c) depicts two electromagnets, however it will be appreciated that in the embodiment described, additional electromagnets may be contemplated, however, due to the cross sectional view are not shown. A bias flux 361 generated by magnet 358 links casing member 353a, 353b with the rotor members including magnet 358 and primary pole piece 354. Similar to FIG. 11(b), the axial equilibrium position of the rotor is shifted from aligning with the pole shoe 353 towards the reverse side of the rotor magnet 358. The same effect of disturbance of active suspension control on passive stability as in FIG. 11(b) is expected to occur, which may be regarded as less preferable than a symmetric configuration like that of FIG. 11(a).

Figure 12:
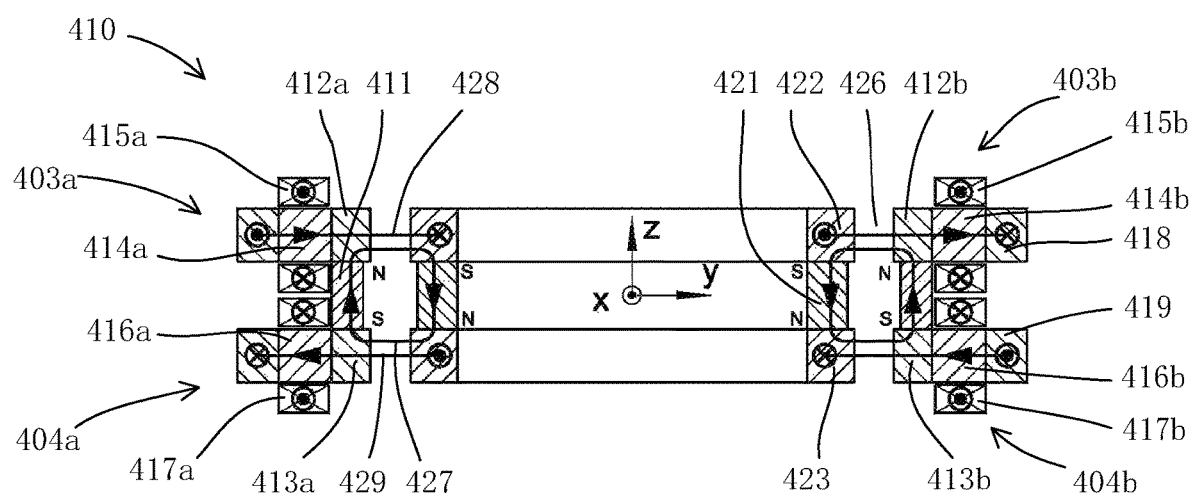
FIG. 12 is a cross-sectional view of the magnetic suspension assembly of a pump in accordance with an embodiment of the present invention.

The configurations of FIGS. 11(b) and 11(c) have advantages in simplicity and cost effectiveness, among others. In order to remedy disturbance of active control force on passive stability, one can combine a pair of those elementary suspension units to form a symmetric configuration that generates active control force in practically pure radial directions. An exemplary embodiment according to this principle is shown in FIG. 12. A magnetic suspension assembly 410 comprises a pair of substantially identical elementary suspension units disposed along the axial direction. The upper and lower unit respectively comprises an annular primary pole piece 422, 423 in the rotor, and a group of electromagnet units 403a, 403b, 404a 404b in the casing. The electromagnets are distributed around the air gap 426, each including an iron core 414a, 414b, 416a, 416b, a coil 415a, 415b, 417a, 417b, and a back yoke 418, 419. The cross-sectional view of FIG. 12 depicts two electromagnets, however it will be appreciated that in the embodiment described, additional electromagnets may be contemplated, however, due to the cross sectional view are not shown. Each primary pole piece 422, 423 may, or may not, have multiple teeth (not shown) formed on its outer surface by cutting out one or more annular grooves on that surface. Each electromagnet unit includes a pole shoe, an iron core, a coil, and a back yoke, the same as in FIGS. 9(a) and (b) and 11. Each pole shoe preferably has substantially same thickness as the rotor primary pole piece, and has same tooth structure on the inner surface as the tooth structure, if any, on the outer surface of the corresponding rotor primary pole piece 422, 423.

The upper and lower elementary hybrid magnetic suspension units are connected together by annular permanent magnets 411, 421. The permanent magnet 411 is sandwiched in between the upper pole shoes 412a, 412b and lower pole shoes 413a, 413b. These pole shoes may advantageously have inner surfaces projected from the inner surface of magnet 411 towards air gap 426. The other permanent magnet 421 is sandwiched in between the rotor primary pole pieces 422, 423. It may advantageously have outer cylindrical surface indented from the outer surfaces of these primary pole pieces. The magnets 411 and 421 have substantially same thickness so that the upper and lower pole shoes 412a, 412b and 413a, 413b are in alignment with the rotor primary pole pieces 422 and 423 respectively. Such configuration serves for focusing magnetic flux into the projected structures adjacent to the air gap 426 and thus obtaining intensified magnetic forces, as discussed above on FIG. 6.

Permanent magnets 411, 421 are magnetized in axial directions opposing to each other. Therefore, they jointly generate bias flux loops 427 that lie in meridian plans of the assembly. The magnetic flux loop 427 serves as the bias flux of both the upper and lower elementary hybrid magnetic suspension units. Moreover, the overall thickness of the rotor assembly, measured from the upper end surface of the primary pole piece 422 to the lower end surface of the primary pole piece 423, is made sufficiently small in comparison with the diameter of the air gap 426. Therefore, according to the above principle of flux loop linkage, passive suspension in axial displacement and tilting is achieved.

The four electromagnet units 403a, 403b, 404a, 404b shown in FIG. 12 are connected in series to work jointly to provide active control of the radial displacement in the y direction. Identical electric current is fed into the coils 415a, 415b, 417a, 417b so that the modulating magnetic flux loops 428, 429 are generated. The symbols with a dot inside a circle and an "x" inside a circle on the cross sections of the rotor primary pole piece 422, 423 and the back yoke 418, 419 indicate modulating flux going out of or into the cross sectional area, respectively. These fluxes passing from one cross sectional area extend their paths along the periphery of the primary pole piece or the back yoke to reach the other cross sectional area on the opposite side about the z axis. As can be seen from FIG. 12, the bias flux 427 and the modulating flux 428 in the air gap 426 on the positive y side go in opposite directions, while these fluxes in the air gap 426 on the negative y side go in the same direction. This leads to a net magnetic force on the rotor primary pole piece 422 in the negative y direction. A similar analysis on the effects of the bias flux 427 and the modulating flux 429 yields a net magnetic force on the rotor primary pole piece 423, also in the negative y direction. Therefore, active control of the radial magnetic force with the mechanism of push-pull modulation of bias flux in the air gap is achieved with the configuration of FIG. 12.

An alternative embodiment that has a stacked structure of the elementary hybrid magnetic suspension units can be made by replacing the rotor members 421, 422, 423 of FIG. 12 with a single annular member of soft iron 441 of FIG. 13. Rotor member 441 allows magnetic flux to pass through along the axial direction, in a similar way as does the magnetic flux of FIG. 12 that passes through rotor magnet 421. Also, the rotor member 441 has two distinct pole edges 442, 443 arranged on the upper and lower end portions of the outer surface, respectively. These pole edges 442, 443 may be formed by simply cutting out an annular groove on the central portion of the outer surface of rotor member 441. The pole edges 442, 443 serve fundamentally the same function of channeling magnetic flux as does the primary pole pieces 422, 423 of FIG. 12, respectively.

Figure 13A:
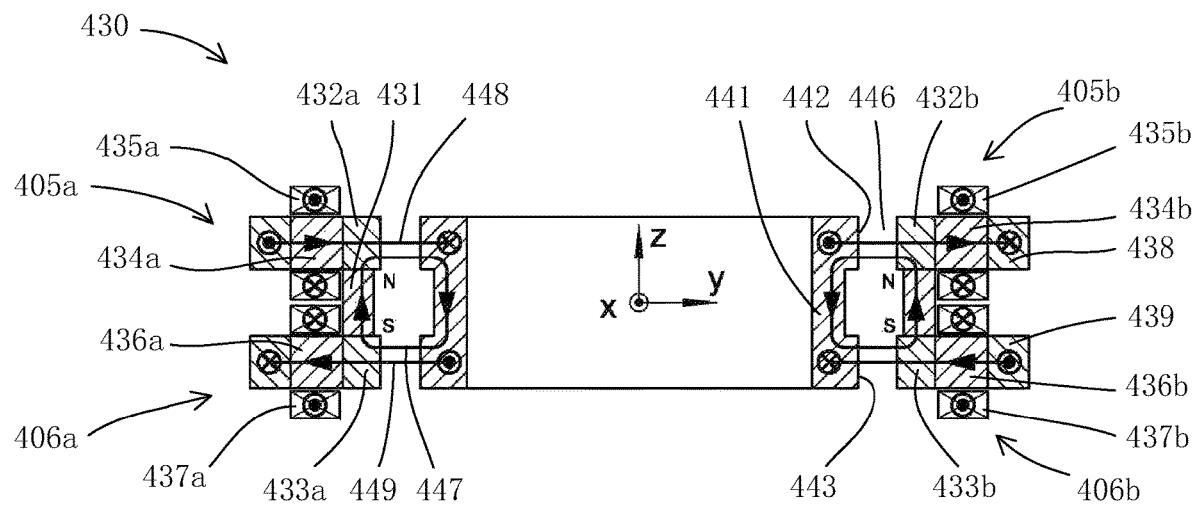
FIGS. 13(a), 13(b) are cross-sectional views of an embodiment of the magnetic suspension assembly of a pump in accordance with an embodiment of the present invention.
Figure 13B:
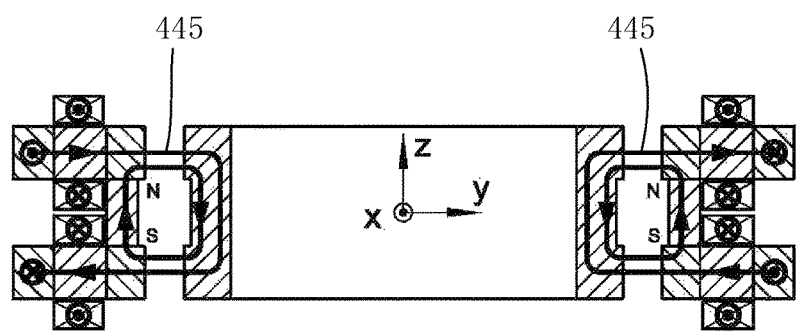

The casing assembly of FIG. 13 has a similar construction as that of FIG. 12. A number of electromagnets are distributed around the air gap 446, each including an iron core 434a, 434b, 436a, 436b, a coil 435a, 435b, 437a, 437b, and a back yoke 438, 439. The cross-sectional view of FIG. 13 depicts four electromagnets, however it will be appreciated that in the embodiment described, additional electromagnets may be contemplated, however, due to the cross sectional view are not shown. The four electromagnet units 405a, 405b, 406a, 406b shown in FIG. 13(a) are connected in series to work jointly to provide active control of the radial displacement in the y direction. Identical electric current is fed into the coils 435a, 435b, 437a, 437b so that the modulating magnetic flux loops 448, 449 are generated. The symbols with a dot inside a circle and an "x" inside a circle on the cross sections of the rotor 441 and the back yoke 438, 439 indicate modulating flux going out of or into the cross sectional area, respectively. Therefore, the permanent magnet 431 generates a bias magnetic flux 447 that forms substantially the same loop as does the bias magnetic flux 427 (FIG. 12) that is jointly generated by the permanent magnets 411, 421 (FIG. 12). On the other hand, electromagnets 405a, 405b, 406a, 406b generate modulating magnetic fluxes 448, 449 that form substantially the same loops as do the modulating magnetic flux 428, 429 (FIG. 12), respectively, provided that the central portion of rotor member 441 is so designed such that the bias magnetic flux 447 causes sufficient saturation therein. If the central portion of the rotor member 441 is not saturated to such extent, then it allows crossover of the modulating magnetic fluxes 448, 449 through the central portion of the rotor member 441. As a result, the modulating magnetic fluxes 448, 449 of FIG. 13(a) may be replaced by magnetic flux 445 of FIG. 13(b). The modulating flux 445 passes from one pole edge 442, 443 to the other pole edge of rotor member 441 along the axial direction in a same meridian plane instead of extending along circumferential direction to the other side of the same pole edge. However, no matter whether the modulating magnetic flux extends through the paths of FIG. 13(a) or the path of FIG. 13(b), the hybrid magnetic suspension device 430 can provide active control in radial directions according to the same mechanism of push-pull modulation of bias magnetic flux as disclosed herein.

The configuration of FIG. 13 employing a single rotor member of soft iron is advantageous with respect to cost effectiveness, among others, in comparison with FIG. 12. However, with the rotor magnet being omitted, less-strong bias magnetic flux is generated, and thus the configuration of FIG. 13 may be associated with less suspension stiffness of passive suspension, less power efficiency due to less magnetic force per unit current of active suspension, among other issues.

Figure 14:
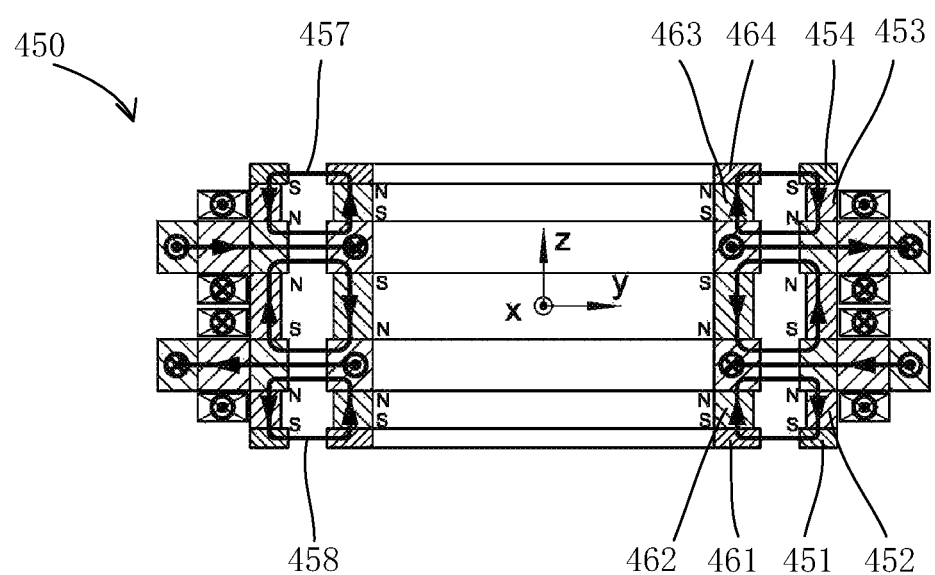
FIG. 14 is a cross-sectional view of an embodiment of the magnetic suspension assembly of a pump in accordance with an embodiment of the present invention.

The hybrid magnetic suspension assembly including, but not limited to, those depicted in FIG. 11, 12 or 13 can be reinforced by adding one or more elementary passive suspension units as described herein to obtain increased suspension stiffness and other required performances. Such an embodiment is shown in FIG. 14, as an example. A hybrid magnetic suspension unit adopted from FIG. 12, is depicted. In addition, a pair of annular permanent magnets 463, 453 is attached respectively to the end surfaces of the rotor primary pole piece and the pole shoes of electromagnet units on the upper end of the hybrid magnetic suspension unit. Also, a pair of annular end pole pieces of soft iron 464, 454 is attached to the other end surface of the magnets 463, 453 respectively. Advantageously, these magnets and end pole pieces may be configured in a way similar to the corresponding members in the upper portion of FIG. 8, which is a typical elementary passive suspension unit of the present invention. In addition, another elementary passive suspension unit comprising magnets 462, 452 and end pole pieces 461, 451 is installed on the lower end of the hybrid magnetic suspension unit of FIG. 14, which may advantageously be configured in a similar way as the lower portion of FIG. 8.

In comparison with FIG. 12, FIG. 14 involves two additional bias flux loops 457, 458 symmetrically located on the both ends of the assembly 450. These flux loops can provide additional stiffness of passive suspension. Moreover, they enhance the magnetic fields in the air gap where modulating flux also passes through, and thus can advantageously contribute to an increase in magnetic force per unit current of active suspension. However, the construction becomes more complicated. In addition, the overall thickness of the rotor assembly 450 of FIG. 14 relative to the air gap diameter has to be sufficiently small in order to ensure passive stability of tilting.

Figure 15:
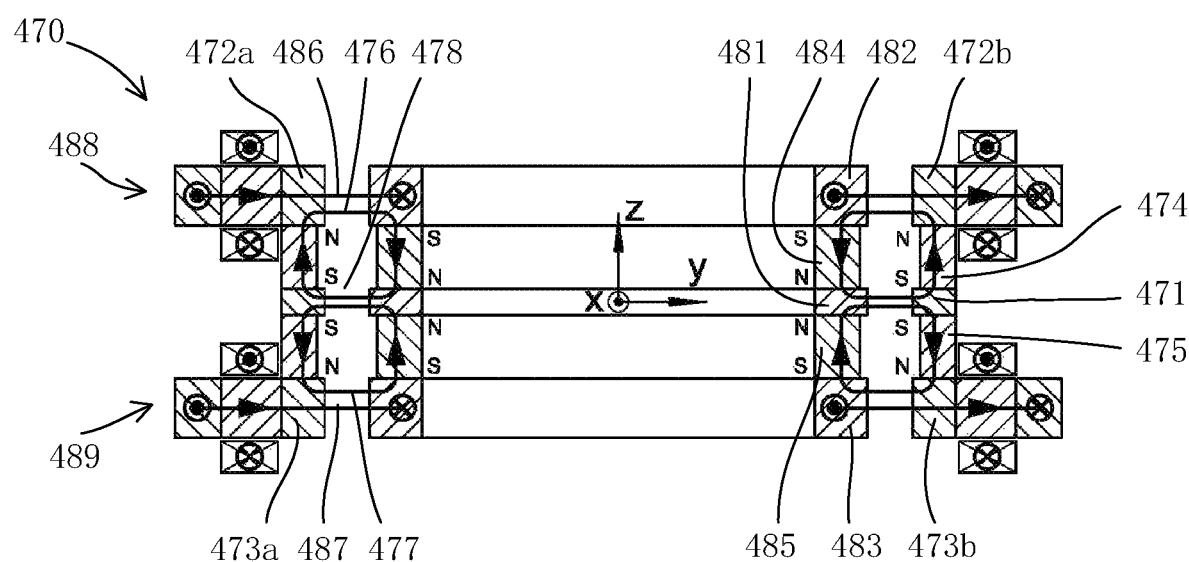
FIG. 15 is a cross-sectional view of the magnetic suspension assembly of a pump in accordance with an embodiment of the present invention.

Whereas in FIG. 14 the additional passive suspension units are mounted to the outward ends of the elementary hybrid suspension units, a passive suspension unit can also advantageously be integrated into the middle of the stacked structure of elementary hybrid suspension units. According to this principle, various other embodiments of the present invention can be made, and one such example is illustrated in FIG. 15. The upper and lower elementary hybrid suspension units of FIG. 12 are adopted for the construction of FIG. 15, but the connection between these units are modified to allow installation of an elementary passive suspension. As shown in FIG. 15, magnetic suspension device 470 comprises a pair of elementary hybrid suspension unit 488, 489 disposed on the upper and lower portion of the device respectively. The upper unit 488 comprises an annular rotor primary pole piece 482 and a plurality of pole shoes 472*a*, 472*b* of the electromagnet units for active control along the y axis. The lower unit 489 comprises an annular rotor primary pole piece 483 and a plurality of pole shoes 473*a*, 473*b* of the electromagnet units for active control along the y axis. The cross-sectional view of FIG. 15 depicts four electromagnets, however it will be appreciated that in the embodiment described, additional electromagnets may be contemplated, however, due to the cross sectional view are not shown. In addition, a passive suspension unit being disposed in the middle of the device 470 comprises an annular first pole member 481 within the rotor, and an annular second pole member 471 within the casing. Both members 471 and 481 are made from soft iron, and preferably have substantially equivalent thickness. The outer cylindrical surface of the first pole 481 and the inner cylindrical surface of the second pole 471 oppose to each other and define an annular air gap 478 for the secondary passive suspension. Three layers of magnetic poles for primary hybrid suspension and additional passive suspension are thus constructed.

An annular permanent magnet 484 is sandwiched in between the rotor primary pole piece 482 and the first pole member 481. Preferably, the outer cylindrical surface of magnet 484 is indented from the outer surfaces of the pole members 482, 481 in order to form a concentration of magnetic field around the poles. Another annular permanent magnet 474 is sandwiched in between the pole shoes 472 and the second pole member 471. Preferably, the inner cylindrical surface of the annular permanent magnet 474 is indented from the inner surfaces of the pole members 472, 471, for the same purpose of magnetic field concentration. Annular permanent magnets 484 and 474 are magnetized along axial directions in opposite to each other. Therefore, they jointly generate a magnetic flux 476 that serves for the bias magnetic flux of the hybrid suspension unit 488. The same flux 476 also serves for the working magnetic flux of the additional passive suspension through the secondary suspension gap 478. The lower portion of device 470 is constructed in symmetry with the upper portion about the x-y plan that passes through the middle of pole members 471, 481. Therefore, another magnetic flux loop 477 is generated by the annular permanent magnets 485, 475, and serves for both the bias flux of the hybrid suspension unit 489 and the working flux of the additional passive suspension unit.

Modulating magnetic fluxes 486, 487 are generated by the electromagnet units in the upper and lower hybrid suspension units respectively. It can be appreciated that whereas the modulating fluxes 428, 429 of the configuration shown in FIG. 12 flow in opposite directions in the meridian plane, the modulating fluxes 486, 487 flow in the same direction, in the configuration shown in FIG. 15.

The pole members 471, 481 may preferably be made sufficiently thin in thickness to generate highly concentrated magnetic field in the secondary passive suspension gap 478. In this manner, the secondary passive suspension can play the major role of passive suspension for axial and tilting stability, as compared to the functions of passive suspension of the hybrid suspension units. The hybrid suspension units, on the other hand, can be optimized for the role of active control for radial stability with less constraint of passive suspension performances. Therefore, the configuration shown in FIG. 15 may be preferable for achieving particular goals of design optimization of a compact magnetically suspended centrifugal pump.

Figure 16:
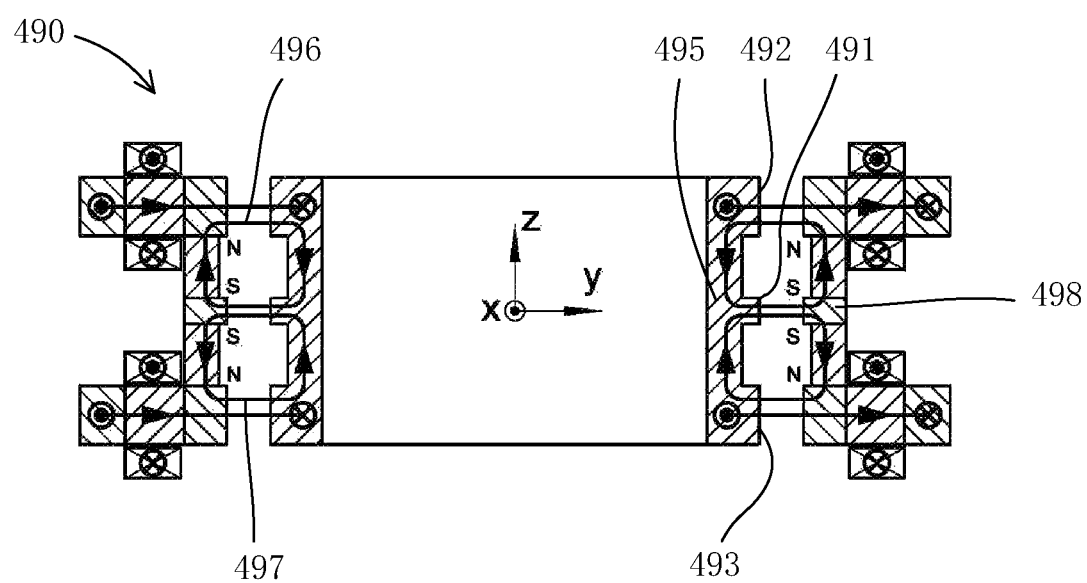
FIG. 16 is a cross-sectional view of the magnetic suspension assembly of a pump in accordance with an embodiment of the present invention.

Analogous to the variation of configurations shown in FIGS. 12-13, an alternative embodiment of the present invention can be made by replacing all of the rotor members of FIG. 15 with a single rotor member 495 of FIG. 16. The rotor member 495 may be made from soft iron and has three pole edges 491, 492, 493 formed on the outer cylindrical surface. The pole edges 492, 493 play same the role as the rotor primary pole pieces 482, 483 of the configuration shown in FIG. 15 coupling with the corresponding pole shoes of the electromagnet units for the hybrid suspension. In addition, the pole edge 491 couples with pole member 498 to define the additional passive suspension gap. Three layers of magnetic poles for the primary hybrid suspension and additional passive suspension are thus constructed in the same manner as that of FIG. 15. The magnetic flux loops 496, 497, although generated solely by permanent magnets in the casing, fulfill the same functions of bias magnetic flux of hybrid suspension and working flux of additional passive suspension.

According to the embodiment shown in FIG. 16, the modulating magnetic fluxes from upper and lower hybrid suspension units would not substantially crossover since they pass through the rotor member 495 in parallel. This is in contrast to the configuration shown in FIG. 13 where modulation fluxes from different layers of the device may crossover as indicated in FIG. 13(*b*). In this sense, the configuration shown in FIG. 16 is preferable, especially when the additional passive suspension is designed as the major contributor to the passive suspension performances, since the magnetic flux in the secondary suspension gap is to a great extent not interfered by the modulating magnetic flux, meaning that the passive suspension is not interfered by the active suspension.

The embodiments of the present invention shown in FIGS. 12-16 have a stacked structure of two layers of electromagnet units so that active control forces at different levels are generated. These forces sum up to result in a net radial force on the rotor, but if the two forces are different in magnitude, then a torque is also induced, which tends to cause the rotor to tilt. Due to the imperfection of materials, dimensional tolerance, operational environment, and other factors involved in practical applications, difference in these forces cannot be entirely avoided. Therefore, such a stacked structure, although preferable for certain applications, may be associated with the issue that active control of radial displacements causes disturbance on passive suspension for tilting stability. This issue may be resolved through proper design considerations such as separating the layers by proper distance, or alternative designs such as that of FIG. 17.

Figure 17A:
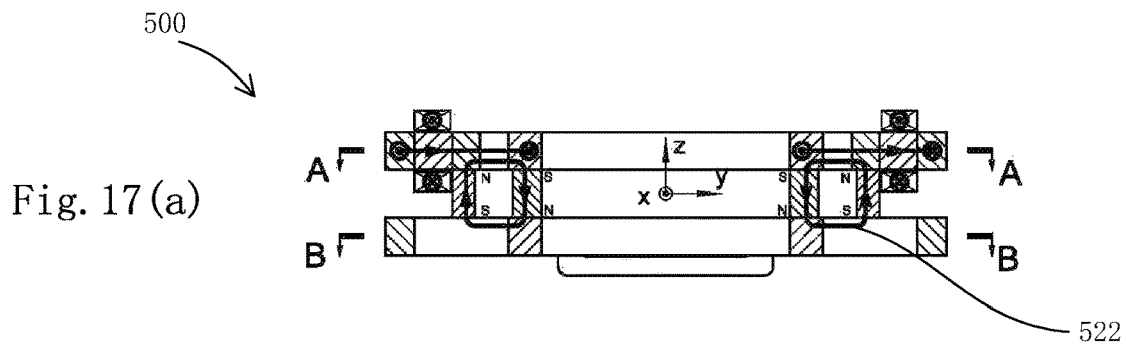
FIGS. 17(a), 17(b), 17(c) are cross-sectional views of the magnetic suspension assembly of a pump in accordance with an embodiment of the present invention.
Figure 17B:
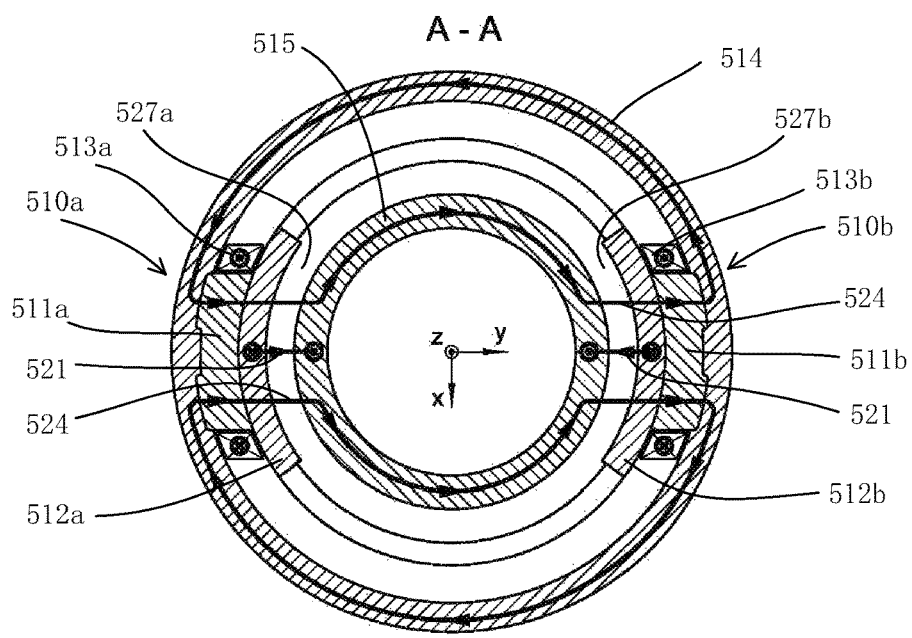

An alternative embodiment of the hybrid magnetic suspension assembly in accordance with this invention, 500, is shown in FIG. 17. It includes a stacked structure with two layers similar to the configuration shown in FIG. 12, but in contrast to that configuration, each layer of the hybrid magnetic suspension comprises only two electromagnet units and the electromagnet units of different layers are circumferentially shifted by 90 degrees to independently control different axis of radial displacements.

FIGS. 17(*b*) and 17(*c*) are respectively cross-sectional views of the upper layer and lower layer of the stacked structure FIG. 17(*a*). Two electromagnet units 510*a*, 510*b* are situated in the upper layer of the stacked structure, each unit consisting of an iron core 511*a*, 511*b*, a pole shoe 512*a*, 512*b*, a coil 513*a*, 513*b*, and a back yoke 514. These units are symmetrically arranged along the y axis and oppose each other. The back yoke 514 of annular continuous soft iron connects the iron cores 511a, 511b of these electromagnets. The pole shoes 512a, 512b face a rotor primary pole piece 515 of annular continuous soft iron. The other group of two electromagnet units 510c, 510d are situated in the lower layer of the stacked structure of FIG. 17, and disposed along the x axis, each unit consisting of an iron core 511c, 511d, a pole shoe 512c, 512d, a coil 513d, 513d, and a back yoke 517. The back yoke 517 of annular soft iron connects the iron cores 511c, 511d. The pole shoes 512c, 512d face a rotor primary pole piece 518 of annular soft iron.

Figure 17C:
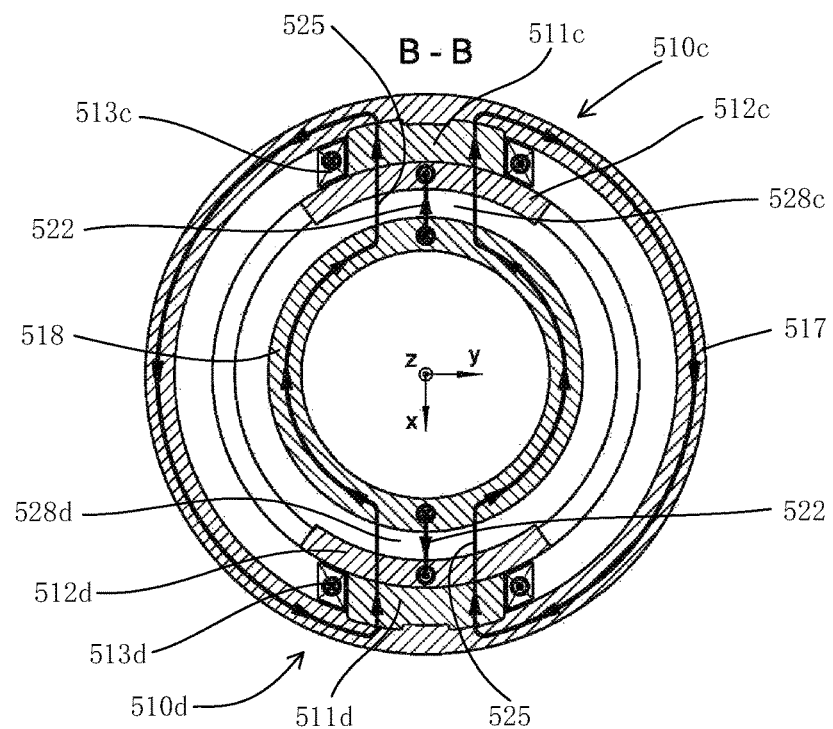

Bias flux loop 522 is generated by annular permanent magnets with the aid of annular rotor primary pole pieces in a same way as that of the configuration shown in FIG. 12. When an electric current is delivered into the coils 513a, 513b, shown in FIG. 17(b), a modulating flux loop 524 is generated. That flux loop 524 passes through the first electromagnet unit 510a, the air gap 527a, a rotor primary pole piece 515, the air gap 527b, the second electromagnet 510b, and closes the loop by passing through the back yoke 514. The combination of modulating flux and bias flux in the two air gaps 527a, 527b along the y axis constitutes push-pull modulation of the bias magnetic flux. Therefore, the group of electromagnet units in the upper layer fulfills the function of active control of the rotor's radial displacement in y axis. A similar analysis applies to the lower layer of the assembly 500, as shown in FIG. 17(c), and readily leads to the group of electromagnets in the lower layer fulfilling the function of active control of the rotor's radial displacement in x axis. When an electric current is delivered into the coils 513c, 513d, shown in FIG. 17(c), a modulating flux loop 525 is generated. That flux loop 525 passes through the first electromagnet unit 510c, the air gap 528c, a rotor primary pole piece 518, the air gap 528d, the second electromagnet 510d, and closes the loop by passing through the back yoke 517. The combination of modulating flux and bias flux in the two air gaps 528c, 528d along the x axis constitutes push-pull modulation of the bias magnetic flux. Therefore, the group of electromagnet units in the lower layer fulfills the function of active control of the rotor's radial displacement in x axis.

Whereas in the embodiment shown in FIGS. 9(a) and (b) the modulating flux for active control along x or y axis passes through the same back yoke and same rotor primary pole piece, the embodiment shown in FIG. 17 works with separate modulating fluxes that passes through different back yoke and different rotor primary pole piece for different axis of control. It can be appreciated that when the rotor of FIGS. 9(a) and (b) deviates from the ideal equilibrium center in an arbitrary radial direction, modulating flux generated by electromagnets for the control of one (say, y) axis may, to more or less extent, enters into the electromagnets for control of the other (say, x) axis. This may cause undesirable coupling between the controls of different axes. In addition, since the pole shoes of the neighboring electromagnet units are situated in the same plane and thus relatively close to each other, magnetic flux leakage between these pole shoes may also cause unacceptable interference between the controls of different axes. On the other hand, in the configuration of FIG. 17, the modulating flux and the corresponding pole shoes for control of one axis and those for control of the other axis are situated in different planes which are separated by a substantial distance. Therefore, the configuration of FIG. 17 can effectively avoid coupling and interference between controls of different axis, and better achieve independent control of radial displacements along each axis.

Moreover, unlike the stacked structures such as those shown in FIGS. 12-16 in which active control of one radial axis relies on two radial forces respectively located in the upper and lower layers of the stacked structure, which may induce a tilting torque, the configuration of FIG. 17 uses a single radial force for control of one radial axis. For example, the radial displacement in the y axis is controlled by merely one force in the upper layer of the stacked structure. Therefore, the configuration of FIG. 17 can also advantageously resolve the issue of disturbance of active control on tilting stability.

According to an embodiment of the present disclosure, the hybrid magnetic suspension assembly can use three electromagnet units to achieve active suspension of radial displacements. An example of such a configuration can be made by replacing the four electromagnet units of FIGS. 9(a) and (b) (also FIGS. 3 through 5) with three units, as shown in FIG. 18. One skilled in the art will appreciated that other embodiments such as those shown in FIGS. 11-17 and FIGS. 22-24 can be modified in the same way to yield alternative configurations which, for purposes of brevity are not discussed herein.

Figure 18A:
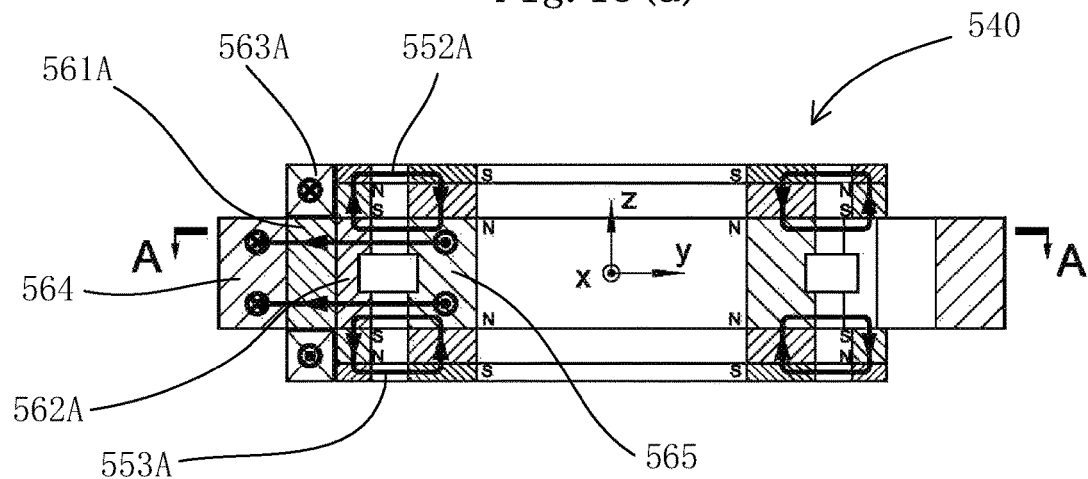
FIGS. 18(a), 18(b) are cross-sectional views of the magnetic suspension assembly of a pump in accordance with an embodiment of the present invention.
Figure 18B:
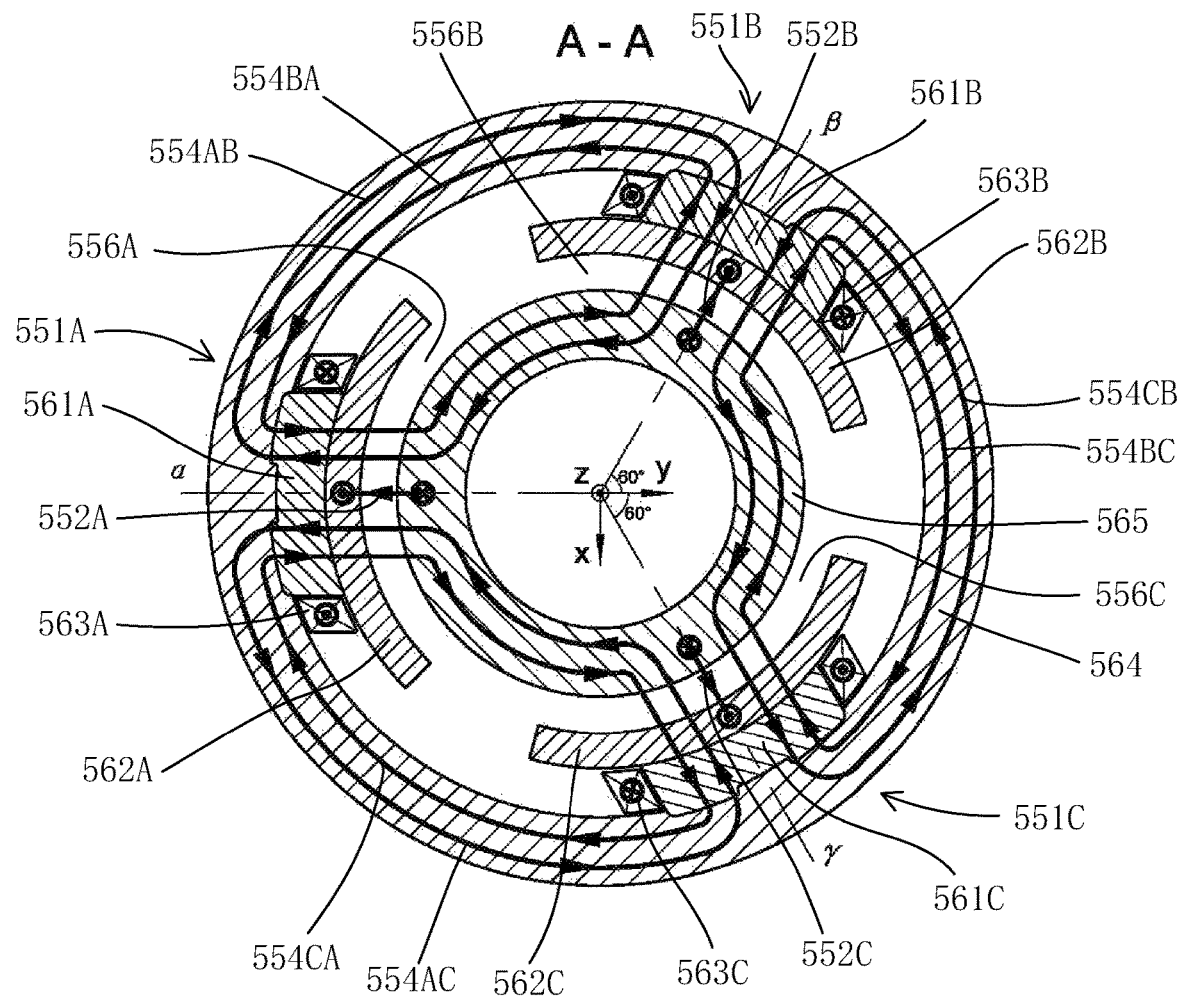

As shown in FIG. 18, three electromagnet units 551A, 551B, 551C are evenly distributed around the annular air gap. Each electromagnet unit 551 consists of an iron core 561, a pole shoe 562, and a coil 563; and an annular back yoke of soft iron, 564, connects the three iron cores. Three axes α, β, γ as indicated in FIG. 18(b), extend from the origin of the coordinate system x-y-z outwards through the iron cores of the electromagnets 551A, 551B, 551C respectively. Each of these axes passes through the peripheral center of the pole shoe surface and coincides with the central axis of the iron core of the corresponding electromagnet. Therefore, magnetic force between any electromagnet and the rotor lies in the direction of the corresponding axis of α, β, or γ. In the particular configuration of FIG. 18, these axes are evenly apart from each other by 120 degrees, although various alternative configurations can be made in accordance with the principle of this disclosure. An annular primary pole piece 565 made of soft iron is disposed in the rotor and opposes the pole shoes of the electromagnets 551A, 551B, 551C across the air gap 556A, 556B, 556C respectively. The rest of the construction of FIG. 18 is fundamentally the same as that of FIGS. 9(a) and (b). Two series of bias flux loops 552, 553 are generated by permanent magnets and are situated symmetrically in the upper and lower portion of FIG. 18(a). The upper or lower portion of the assembly contributes a substantially identical magnetic force because of constructional symmetry, and a sum of the forces yields the overall force on the rotor. Only the force at the upper portion will be discussed below.

The three coils of the electromagnets are connected in such a way that electric currents flowing into these coils are balanced. For example, the Y connection or Delta connection that is commonly used in three-phase electric machinery may be employed. Correspondingly, the sign of electric current in a coil is defined such that a positive current produces magnetic flux passing through the core of the coil outwards from the origin of the coordinate system. Now, suppose electric currents $I_A$, $I_B$, $I_C$ are supplied into coils 563A, 563B, 563C respectively, and these currents satisfy $$I_A+I_B+I_C=0 \quad (3)$$

The current $I_A$ in coil 563A produces two symmetric groups of magnetic flux 554AB and 554AC as indicated in FIG. 18. The magnetic flux 554AB goes from the rotor primary pole piece 565 which possess a reference magnetic potential, and passes through air gap 556A in an outward direction (corresponding to positive current $I_A$). The magnetic flux 554AB continues to flow outward through the pole shoe 562A and the iron core 561A of the electromagnet 551A, and enters the back yoke 564 which possesses a substantially uniform magnetic potential over the circumference. The magnetic flux then goes along the periphery of the back yoke 564 and reaches one end of the electromagnet 551B. It then passes through the iron core 561B and the pole shoe 562B of electromagnet 551B in an inward direction, and then through the air gap 556B. It finally enters into the rotor pole piece 565 and completes the loop. The other magnetic flux produced by the current $I_A$ in coil 563A, 554AC, also passes through electromagnet 551A in outward direction, but it then goes through electromagnet 551C before completing the loop. In a same way, each of currents $I_B$, $I_C$ in the other two electromagnet units produces a couple of magnetic flux loops, each linking a pair of electromagnets. A total of 6 groups of such flux loops are produced. These flux loops are designated by the numeral 554 followed by two suffix alphabets, the first alphabet representing the electromagnet that energizes the flux loop, and the second alphabet representing the electromagnet that the flux loop also passes through, i.e. links with. For example, flux loop 554AB is energized by the electromagnet 551A and it also links the electromagnet 551B. For another example, the flux loop 554BA is energized by the electromagnet 551B and it also links the electromagnet 551A. The flux loop 554AB and 554BA overlap but flow in opposite directions. They sum up as signed numbers and results in the net magnetic flux along that common path.

Figure 19:
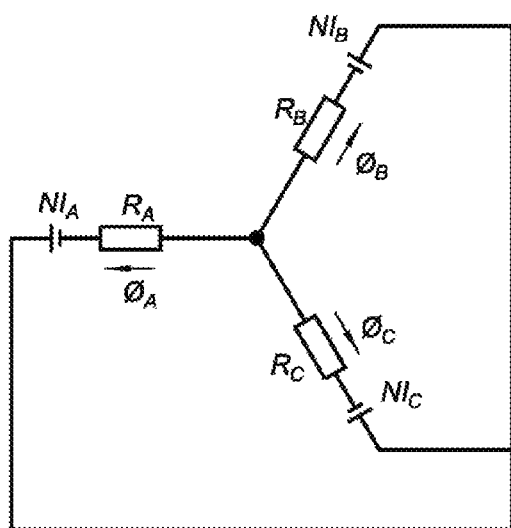
FIG. 19 is the magnetic circuit for the electromagnet units of FIG. 18 in accordance with an embodiment the present invention.

The above flux loops and the associated magnetic components of FIG. 18 can be modeled with the magnetic circuit of FIG. 19. The magnetic reluctance of the soft irons is assumed negligible, so the rotor primary pole piece 565 and the back yoke 564 can be modeled as single points. The $R_A$, $R_B$, $R_C$ represent the reluctance of air gaps 556A, 556B, 556C respectively. The $NI_A$, $NI_B$, $NI_C$ represent the magnetomotive forces of the electromagnets 551A, 551B, 551C respectively, where N is the number of turns of the coil and I is the electric current in the coil. The $\Phi_A$, $\Phi_B$, $\Phi_C$ are magnetic flux through the corresponding air gaps in the circuit, generated by the electromagnets. This magnetic circuit leads to the following equation $$\Phi_A + \Phi_B + \Phi_C = 0 \quad (4)$$

Also, analysis of magnetomotive forces for each branch of the magnetic circuit yields that magnetomotive force rise in the electromagnet equals to magnetomotive force drop over the corresponding air gap, for example, $NI_A = \Phi_A R_A$. Also note that the three air gaps have the same dimensions, and thus $R_A = R_B = R_C$. Therefore, Equation (4) is in consistent with Equation (3).

The bias flux loops 552 include three groups 552A, 552B, 552C that respectively pass through the air gaps 556A, 556B, 556C. They produce the same flux density in these air gaps because of the constructional symmetry of the configuration shown in FIG. 18. Therefore, the bias magnetic flux density in any air gap is denoted as B.

Suppose the magnetic flux density in the air gaps 556A, 556B, 556C due to the modulating fluxes $\Phi_A$, $\Phi_B$, $\Phi_C$ are $\Delta B_A$, $\Delta B_B$, $\Delta B_C$ respectively. Since magnetic flux density is in proportion to magnetic flux, the following relationship can be obtained from Equation (4)

$$\Delta B_A + \Delta B_B + \Delta B_C = 0 \quad (5)$$

According to magnetics theory, the magnetic force on a surface of highly permeable magnetic material is in proportion to the product of the square of flux density on the surface and the surface area. Therefore, the magnetic forces on the rotor, $F_A$, $F_B$, $F_C$, in air gaps 556A, 556B, 556C from electromagnet units 551A, 551B, 551C, respectively, are $$F_A = k \cdot S \cdot (B + \Delta B_A)^2 \quad (6)$$

$$F_B = k \cdot S \cdot (B + \Delta B_B)^2 \quad (7)$$

$$F_C = k \cdot S \cdot (B + \Delta B_C)^2 \quad (8)$$

where S is the surface area of the inner surface of the electromagnet pole shoe, and k is a constant.

These forces are directed along the $\alpha$, $\beta$, $\gamma$ axes shown in FIG. 18(b), respectively, with positive force pointing outwards from the center of the assembly.

The net signed force in the $\alpha$ axis is $$F_\alpha = F_A - F_B \cos(60°) - F_C \cos(60°) \quad (9)$$

From Equations (5) through (9), the force can be represented as:

$$F_\alpha = 3kSB\Delta B_A + \frac{1}{2}kS(\Delta B_A^2 + 2\Delta B_B \Delta B_C) \quad (10)$$

The bias flux is generated by permanent magnets and the modulating flux is produced by electromagnets. The permanent magnet creates much higher magnetomotive potential rise than electromagnet does. Therefore, bias flux density B is usually much greater than any of the modulating magnetic flux densities $\Delta B_A$, $\Delta B_B$, or $\Delta B_C$. Equation (10) can be approximated with $$F_\alpha = 3k \cdot S \cdot B \cdot \Delta B_A \quad (11)$$

The air gap flux density $\Delta B_A$ generated by electromagnet unit 551A is in proportion to electric current in that electromagnet, $i_A$, as long as the corresponding magnetic circuit is not saturated. Therefore, (11) can be rewritten as $$F_\alpha = c \cdot B \cdot i_A \quad (12)$$

where c is a constant.

This shows a linear relationship between the magnetic force along the $\alpha$ axis and the electric current flowing into the electromagnet unit that resides on the $\alpha$ axis, similar to the linear relationship of Equation (2). Further, the linear relationship is resulted from summation of force $F_A$ towards the positive $\alpha$ axis, and projections of forces $F_B$, $F_C$ towards the negative $\alpha$ axis. A push-pull mechanism similar to that involved in Equation (1) can be observed.

By symmetry, similar expressions are obtained for the magnetic forces along the $\beta$ and $\gamma$ axes, as follows $$F_\beta = c \cdot B \cdot i_B \quad (13)$$

$$F_\gamma = c \cdot B \cdot i_C \quad (14)$$

Magnetic forces $F_x$ and $F_y$ along the x and y axes, respectively, of FIG. 18 can be obtained through a linear transformation from Equations (12) through (14). Therefore, in a configuration of FIG. 18 where bias flux density is much greater than modulating flux density, magnetic force for active control of any of the two radial displacements is in linear relationship with the electric currents in the electromagnet units. This attribute of active control forces is highly desirable, the same as in the case of the embodiments such as FIGS. 9(a) and (b) where four electromagnet units are employed, since it facilitates application of linear control algorithms, among many other potential advantages. Also, the linear relationship is a result of the push-pull modulation of the bias magnetic flux in the air gap, which is fundamentally the same mechanism involved in the other embodiments of the hybrid magnetic suspension disclosed in this invention.

The above discussion illustrated the general principle and construction of the hybrid magnetic suspension assembly equipped with four or three electromagnet units. According to the same fundamental principle, other numbers of electromagnet units, evenly or unevenly disposed around the air gap, can be employed to yield various alternative designs by one skilled in the art. The above discussion also illustrates the method for deriving expressions of active control force in terms of electric current and bias magnetic flux density. This method and resultant expressions can be used to understand the mechanism of magnetic flux modulation in accordance with this invention, so that various design configurations especially those with an advantageous linear relationship for active control, can be readily conceived by those having skills in the field.

The pump 10 of FIGS. 1-3 is exemplified with a magnetic suspension assembly 60 consisting of a casing assembly 61 mounted within an exterior casing 16 of a housing 12 as illustrated in FIGS. 3-5. An alternative embodiment may configure the magnetic suspension assembly 60 in the inner portion of the pump so that the casing assembly 61 is mounted within central post 15, and the rotor assembly 62 is flipped over to the inner side of the rotor 30 so that the casing assembly 61 and the rotor assembly 62 oppose each other across the air gap 43 of FIG. 3. Such a configuration can be made to achieve the same fundamental functions of magnetic suspension in this invention by simply reversing the original configuration about the air gap. Specifically, in the alternative configuration, the teeth 87, 88 on the pole shoes 83 of the electromagnets is disposed adjacent to the air gap 43, and the iron core 92 extends inward from the pole shoes and connects the back yoke 95 that constitutes the innermost member of the magnetic suspension assembly. The other components in the casing assembly 61, as well as the rotor assembly 62, are flipped inside-out in the same manner. Besides, this method of constructing a magnetic suspension unit in the inner portion of the pump can be equally applied to any of the other embodiments such as those of FIGS. 11-18 to yield additional alternative embodiments of the present disclosure.

The structural and hydraulic features of the pump, as disclosed herein, are not to be taken in a limited sense, and they are made merely for the purpose of illustrating the general principle and construction involved in the present invention, especially with respect to the magnetic suspension. For example, the chamber of the exterior casing 16 of the configurations shown in FIGS. 1-3 may not be necessary if the magnetic suspension unit is disposed in the inner portion of the pump, as discussed above. On the other hand, the central post 15 may not be necessary for successful practice of the present invention, as long as the components of magnetic suspension and motor can be disposed within the other portion of the housing. In addition, the rotor 30 may take other shapes for its inner and/or outer surfaces such as a conical shape rather than the right cylindrical surfaces as illustrated in FIG. 2.

Figure 20:
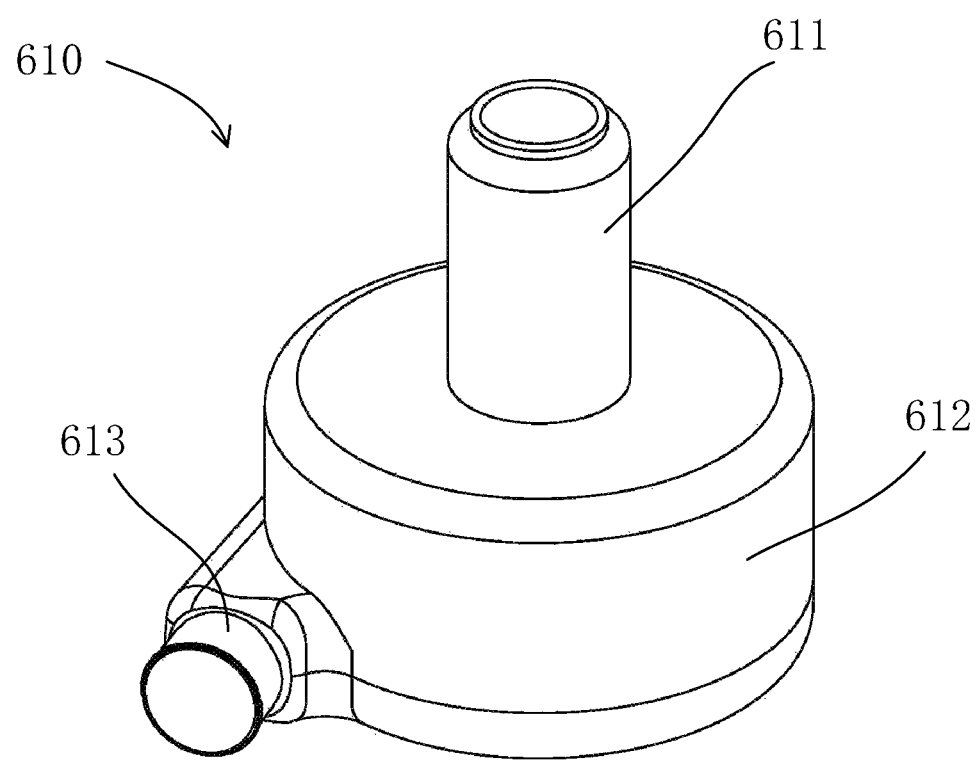
FIG. 20 is a top front perspective of another pump in accordance with an embodiment of the present invention.
Figure 21:
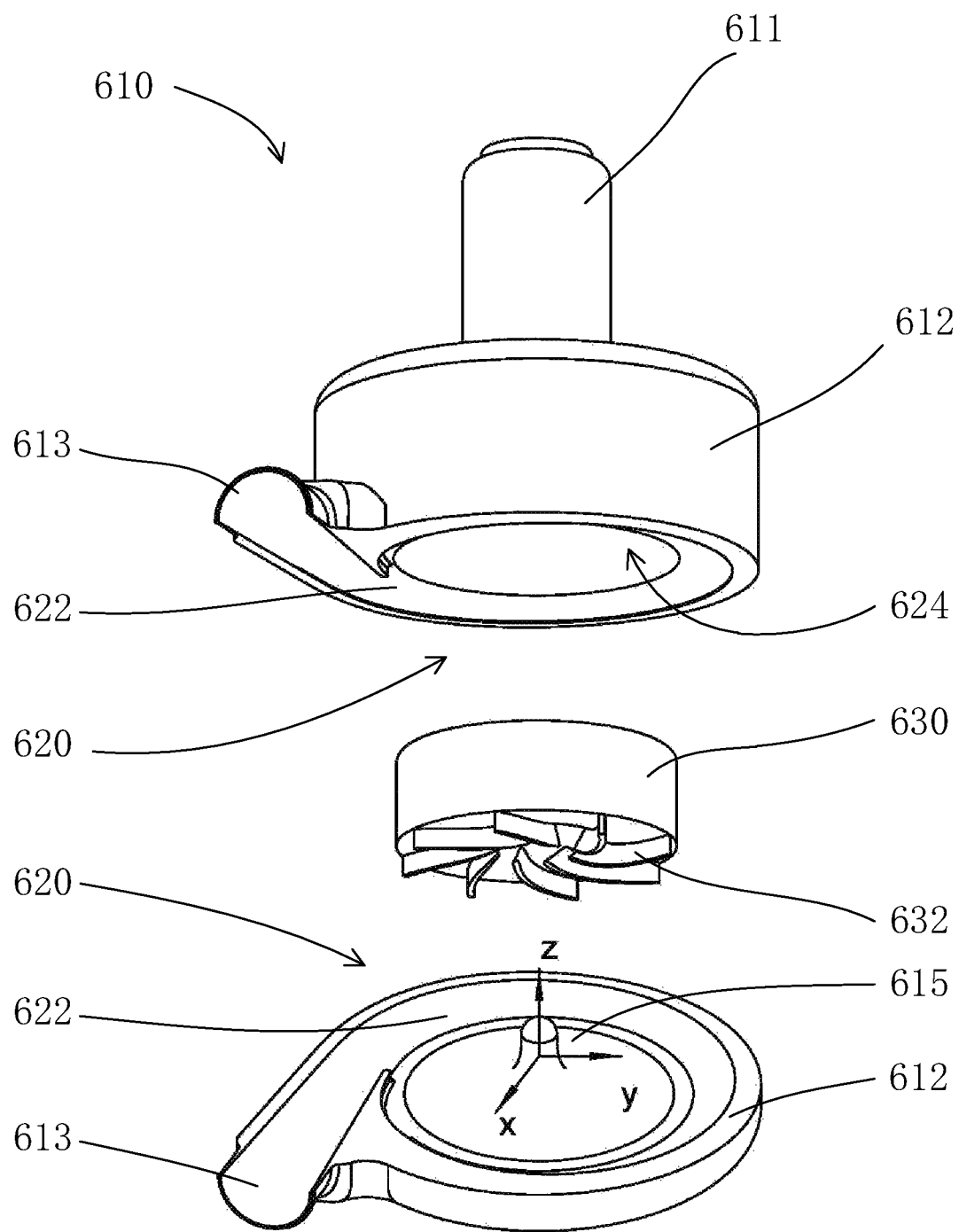
FIG. 21 is an exploded view of the pump of FIG. 20, showing the pump's interior construction for fluid flow through the pump.
Figure 22:
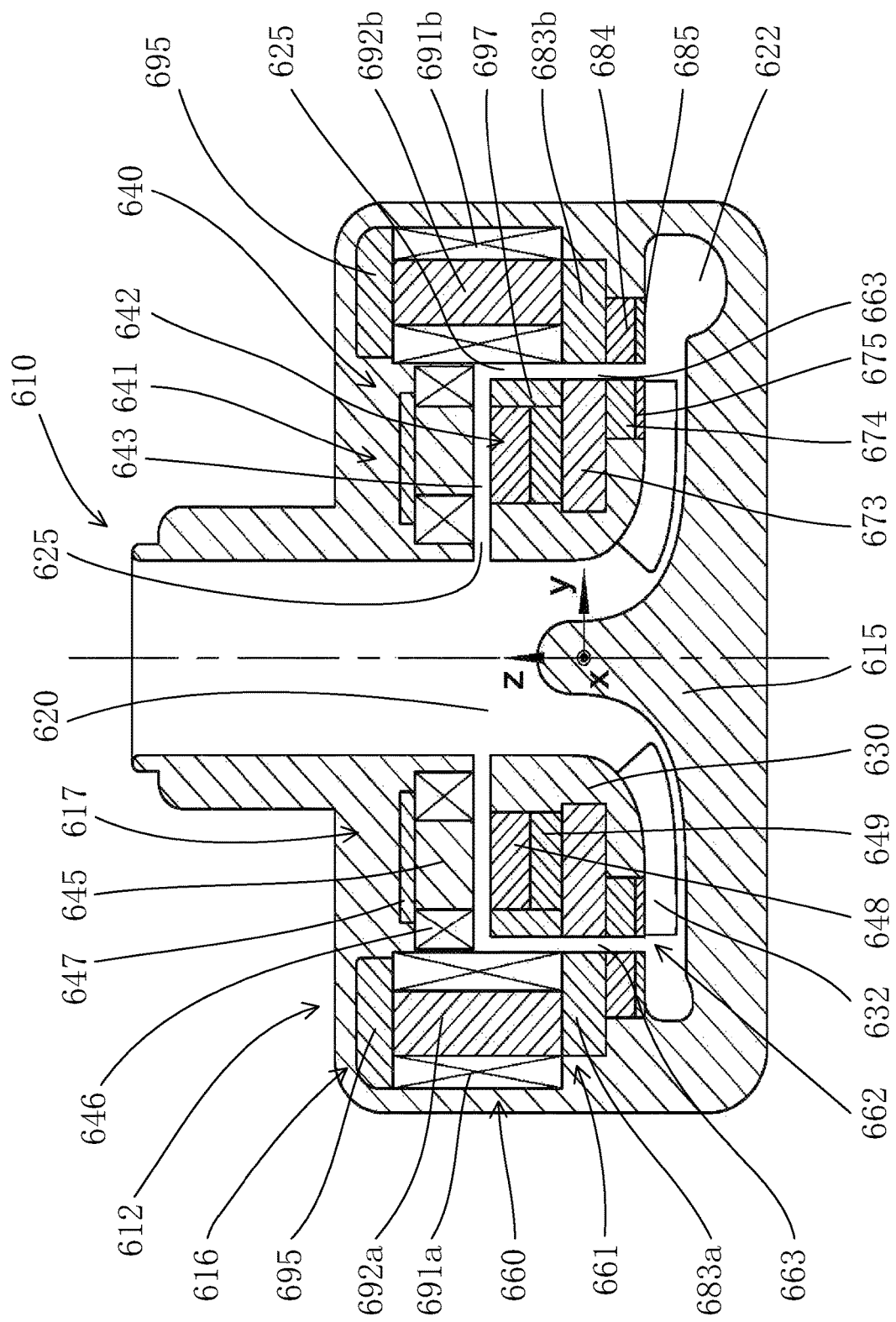
FIG. 22 is a front cross-sectional view of the pump of FIG. 20, showing the constructions of the rotor and the housing with emphasis on the magnetic suspension and electric motor.

FIGS. 20-22 illustrate an alternative pump 610 in accordance with an embodiment of the present disclosure. It includes a housing 612 with an inlet 611 to receive working fluid into the pump and an outlet 613 to discharge the pressurized fluid out of the pump. The side towards the inlet 611 is referred to herein as the front side of the pump 610 and the opposite side as the rear side. The housing 612 has a continuous inner wall that borders an interior chamber 620, which communicates with the inlet 611 and outlet 613. The chamber 620 is enclosed by a cylindrical side surface, a substantially flat end surface on the front side of the pump 610, and a curved end surface on the rear side of the pump 610, corresponding to a nose cone structure 615 that projects from the pump rear end towards the pump inlet 611. The housing 612 also has an outer wall, which together with the inner housing wall form a space therebetween for mounting stationary components of an electric motor and magnetic suspension. Particularly, an exterior casing 616 is formed in between the cylindrical surface of the chamber 620 and the outer cylindrical wall of the housing 612, and an end casing 617 is formed in between the end surface of chamber 620 and the front-end outer wall of the housing 612. A volute 622 is constructed on the periphery of the interior chamber 620 for collecting fluid discharged from pump impeller 632, and communicating with the pump outlet 613.

A rotor 630 is disposed within the pump interior chamber 620 and is fully magnetically suspended without any physical contact with the surface of the chamber 620. An impeller 632 consisting of a plurality of blades is mounted on the rotor 630 to transfer energy to the working fluid. Unlike the configuration of FIGS. 2 and 3 where the impeller is attached to the front end of the rotor, the impeller 632 is attached to the rear end of the rotor 630, which may be conventionally named a reverse impeller. The nose cone 615, together with the rear surface of pump interior chamber 620, is constructed to form a streamlined flow path for the working fluid to pass through the impeller blades 632 radially outward. The rotor is magnetically suspended so that an "L" shaped flow gap 625 is formed in between the front end surfaces of the rotor 630 and the pump interior chamber 620 for one arm of the "L", and in between the outer cylindrical surface of the rotor 630 and the inner cylindrical surface of the pump interior chamber 620 for the other arm of the "L". The mainstream of fluid flow passes from the inlet tubing 611 through the impeller 632 into the volute 622. In the meanwhile, a secondary flow is generated due to pressure gradients through the "L" shaped gap 625. The fluid of the secondary flow passes into the outer cylindrical gap towards the front end, and then flows inward in the annular end gap, and finally merges into the main flow inside the inlet tubing. The secondary flow takes a fractional amount of the main flow but plays an important role in washing the blood-contacting surfaces in the suspension gap 625 to prevent blood clotting, among other advantages in handing stress-sensitive fluids. It can be appreciated that this secondary flow path, like the secondary flow path of FIG. 3, is straightforward and free from a zigzag structure or any other obstructive feature in the flow channel so that unimpeded wash out on the entire rotor surface can be achieved.

Figure 23:
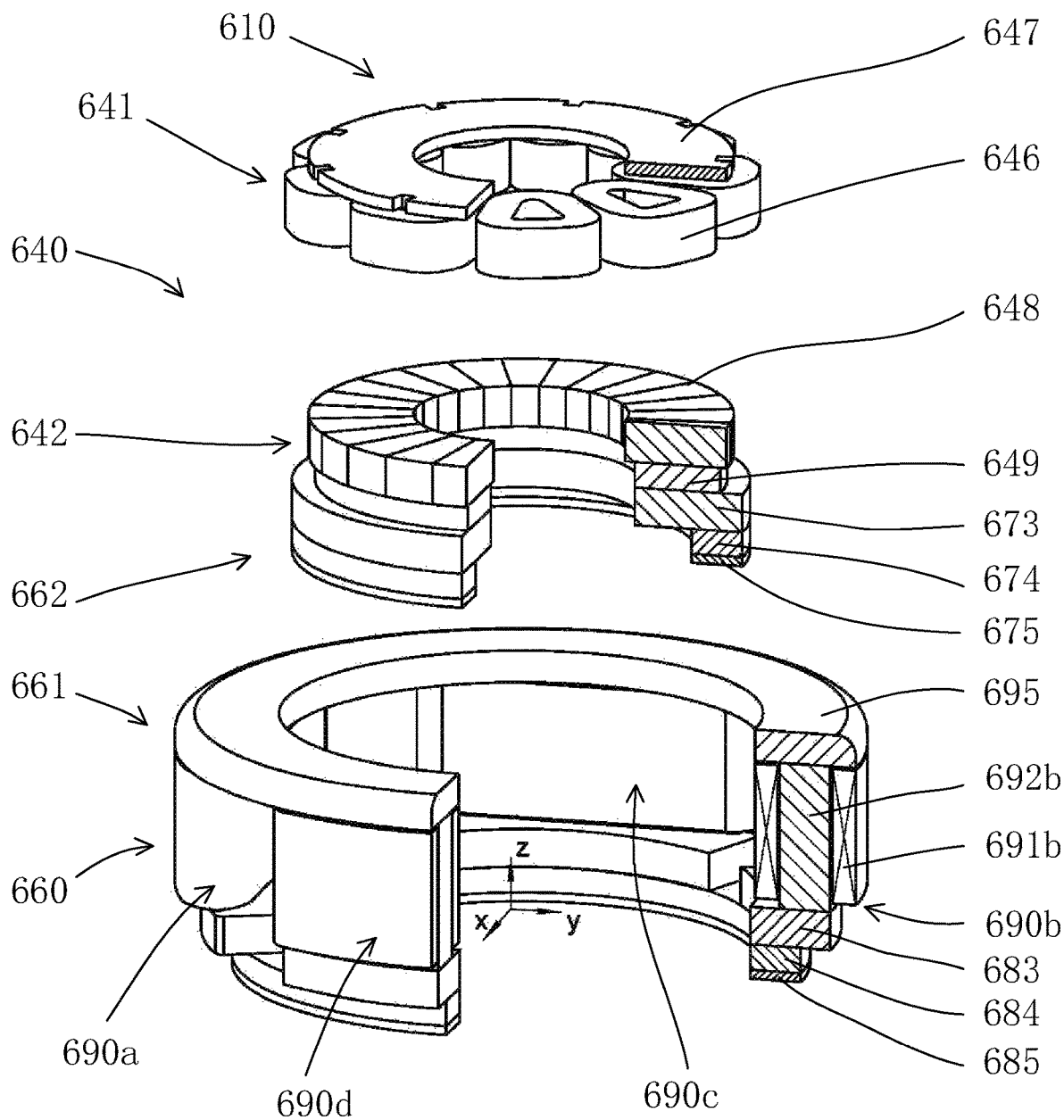
FIG. 23 is an exploded isometric view of the assemblies of the magnetic suspension and the electric motor in the pump of FIG. 20, shown in partial cross-sectional views.

According to an embodiment of the present invention, an electric motor 640 including a stator assembly 641 and a rotor assembly 642, is disposed within the front end portion of the pump, as shown in FIGS. 22 and 23. Unlike the motor 40 in the pump 10 of FIG. 3 which works with magnetic flux in a radial direction, the motor 640 is an axial flux motor that works with substantially axial magnetic flux. The rotor assembly 642 consists of a plurality of permanent magnet pieces 648 evenly distributed in an annular space of the front end of rotor 630. Each magnet piece is preferably made into a shape like a fan so that these pieces can be assembled side by side circumferentially to form a solid ring centered about the rotational axis of rotor 630. These magnet pieces are magnetized with regularly varying polarities to form magnetic poles in axial directions, which create the working magnetic flux passing through the air gap in axial direction. The variation of polarities may follow any pattern that is known to ones having skill in this field, for example, a Halbach array configuration that can advantageously create enhanced magnetic field on the air gap side. An annular piece of soft iron 649 may preferably be disposed on the back end of the magnet ring to serve as a back iron for fixing the magnet pieces in place and also completing the magnetic flux loop of the magnetic poles. However, it can be replaced with a nonmagnetic material or may not be needed without deviating from the general principle of this invention.

Motor stator 641 is mounted within the end casing 617 of the housing 612 closely adjacent to the air gap 643. It includes a plurality of motor coils 646, evenly distributed circumferentially in the annular space opposing to the rotor magnet ring. The coil axis is orientated substantially parallel with the rotor's rotational axis so that the rotor magnetic flux passes through the end surface area enclosed by the coil turns, or the flux links the coils. The coils 646 are connected into groups of windings of multiple phases, for example 3 phases, in a way commonly known to one skilled in the art. The coils 646 may be wound on cores 645 of soft iron to improve power efficiency of the motor. However, they may alternatively be wound on a core of nonmagnetic material, or without a core, in order to avoid or alleviate magnetic attracting force between the stator iron and rotor magnets. This is especially an advantage for a magnetically suspended rotor since the attracting force creates negative stiffness in axial direction that has to be compensated by positive stiffness provided by the magnetic suspension, which requires additional volume and weight of the magnetic suspension assembly, among other potential issues. Although the coils 646 shown in FIGS. 22 and 23 are distinctly wound around cores 645, alternatively, they can be constructed without a core and arranged in an overlapped manner with one side of a coil residing in the core area of another coil. This adds more flexibility in making use of space for a compact device. An annular plate of soft iron, the stator back yoke 647, may be disposed on the back side of the stator coils 646 to increase magnetic flux linking the coil turns. In addition, a structure of partial iron cores that fills merely a portion of thickness of the coil core space may be made on the end surface of the back yoke 647, to further increase the magnetic flux linkage and bring about increased efficiency. However, these structural features may not be needed, especially if they cause unacceptable magnetic attracting force between the motor stator and rotor.

It should be noted that the general principle and constructional features of the radial flux motor and axial flux motor disclosed herein can lead to other preferred configurations of electric motor of this invention. For example, the motor may possess an air gap of a straight conical or curved conical shape, so that the working magnetic flux passing through the air gap forms an angle with respect to the rotational axis of the rotor. In this way, the electric motor as discussed above can be readily adapted to various configurations of fluid pathway and magnetic suspension for handling stress sensitive fluids, by those having skill in the field.

Figure 24:
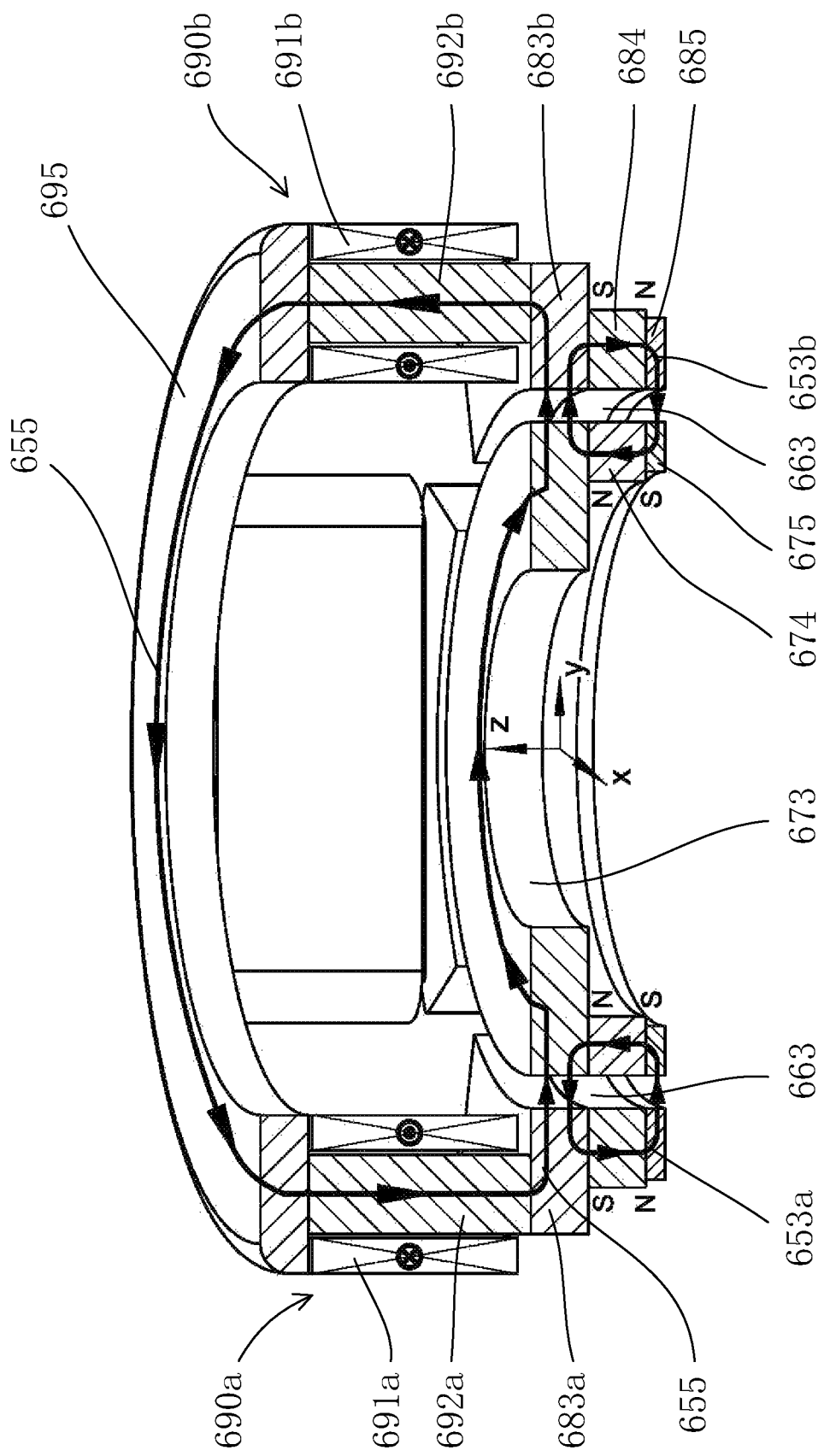
FIG. 24 depicts the magnetic suspension assembly in the pump of FIGS. 20 through 23.

As shown in FIGS. 22 through 24, the magnetic suspension assembly 660, in accordance with an aspect of the present disclosure, includes a rotor assembly 662 and a casing assembly 661. The casing assembly 661 is mounted within the exterior casing 616 of the pump housing 612. The rotor assembly 662 is mounted on the outer side of the pump rotor 630. The magnetic suspension assembly 660 is a hybrid structure of permanent magnet and electromagnet for passive and active suspensions according to the principle described in this disclosure, for example, in FIGS. 9(a) and (b).

The rotor assembly 662 consists of a primary pole piece 673, which is an annular plate of soft iron having an outer cylindrical surface opposing the air gap 663. An annular permanent magnet 674 magnetized across its thickness is mounted on the rear end surface of the primary pole piece 673. In an alternative configuration (not shown), another annular magnet is mounted on the front end surface of the primary pole piece to form a symmetric structure similar to the magnetic suspension construction of FIGS. 9(a) and (b). This may enhance bias magnetic flux at the cost of increased volume of the pump. An end pole piece 675, an annular plate of soft iron, is attached to the other end surface of permanent magnet 674 to serve for focusing magnetic flux into a concentrated area in air gap. The end pole piece 675 may not be needed, however, as long as sufficient suspension stiffness can be obtained, for example.

The casing assembly 661 consists of four substantially identical electromagnet units 690a-d, evenly distributed around the periphery of the assembly. Each electromagnet 690a-d includes a pole shoe 683a-d which is primarily a circumferential segment of an annular soft iron. The four pole shoes 683a-d are disposed around the annular space, separated by gaps in between the neighboring pole shoes. The pole shoe 683a-d has an inner cylindrical surface opposing the rotor primary pole piece 673, preferably with substantially equivalent thickness of the latter. An annular permanent magnet 684 magnetized across its thickness is installed on the rear end surfaces of the pole shoes 683a-d. An end pole piece 685 of annular soft iron is mounted on the rear end of permanent magnet 684. The magnet 684 and end pole piece 685 are preferably of substantially equivalent thickness as those of the opposing members 674, 675, respectively. A symmetric configuration (not shown) that also includes a permanent magnet and/or end pole pieces mounted on the front end surfaces of the pole shoes 683a-d, corresponding to the above mentioned alternative rotor configuration, may be employed as alternative embodiments of this invention.

Each electromagnet unit 690a-d also includes an iron core 692a-d, a coil 691a-d that is wound around the iron core 692a-d, and a back yoke 695 that is shared by all electromagnet units. Iron core 692a-d is primarily a cubic piece made of soft iron, with cross sectional shape of circular, rectangular with rounded corners, or any other suitable shape commonly known to one skilled in the art. One end of the iron core 692a-d is attached to an end surface of pole shoe 683a-d, and the other end of the iron core 692a-d is attached to an end surface of back yoke 695, which is an annular plate of soft iron and serves as the base circle to structurally connect all electromagnet units together. Unlike the iron cores 92a-d of FIGS. 9(a) and (b) that extend radially like spokes of a wheel, the iron cores 692a-d extend axially like legs that connect the base circle and top members (pole shoes). Magnetically, the back yoke 695 connects one electromagnet to the opposing electromagnet residing on the same radial axis (e.g. 690a and 690b on y axis) so that a pair of electromagnets works jointly for control of displacement in that axis. It should be appreciated that although the construction of electromagnet 690 of FIG. 24 for pump 610 (FIG. 22) and the construction of the electromagnet unit 90 of FIGS. 9(a) and (b) for pump 10 (FIG. 3) appear different from each other, the general topology and magnetic circuit remains substantially similar Both electromagnets are constructed with the same fundamental building blocks including the pole shoe, iron core and back yoke, in a fundamentally same way of connecting these building blocks to form a magnetic circuit. One construction can be viewed as a result of bending and stretching the other construction without changing the structure of the magnetic circuit. However, a different aspect ratio of the magnetic suspension assembly is obtained by such a different configuration so that the assembly 60 best fits into the pump 10 of FIG. 3 and the assembly 660 best fits into the pump 610 of FIG. 22. In that way, each individual pump can be optimized for the smallest overall pump size. Based on this discussion, various other embodiments of the magnetic suspension can be conceived according to the general principle of this invention by one skilled in the art, to best utilize the available space within a pump housing to create the most compact pump.

The magnetic suspension assembly 610 fulfills the function of passive suspension according to the same principle of magnetic flux linkage as the other embodiments of the present invention. Referring to FIG. 24, permanent magnets 674 and 684 together generate a group of magnetic flux loops 653*a-b*. Each flux loop 653*a-b* links the rotor members including permanent magnet 674, end pole piece 675, and primary pole piece 673, with the casing members including the permanent magnet 684, the end pole piece 685, and the electromagnet pole shoe 683*a-b*. These rotor members and casing members oppose to each other across a radial air gap 663. In addition, the overall thickness of the rotor assembly including members 673, 674, and 675 is sufficiently small in comparison with the diameter of the air gap 663. Therefore, the flux loop 653 has the attribute of flux loop linkage as defined herein and thus can provide axial and tilting stability. Note that while the FIG. 24 shows magnetic flux loops 653*a-b* and pole shoes 683*a-b* due to the cross-sectional view, one skilled in the art will appreciate two additional flux loops and pole shoes are present in the embodiment, but are not shown in the cross-section.

The active suspension is achieved with the same mechanism of push-pull modulation of bias flux in air gap as the other embodiments of this invention. As shown in FIG. 24, a group of bias flux loops 653*a-b* are generated by permanent magnets 674, 684. Two electromagnet units 690*a*, 690*b* work together for active control in y axis; and two other electromagnet units 690*c*, 690*d* work together for active control in x axis. Without loss of generality, only control in y axis is discussed below. Coils 691*a*, 691*b* are connected in series so that when electric current is supplied, they jointly generate a magnetic flux loop 655, i.e. the modulating flux. The flux loop 655 is completed by passing through the perimeters of the rotor primary pole piece 673 and of the back yoke 695, in addition to the iron core 692*a* and the pole shoe 683*a* of the electromagnet unit 690*a*, the iron core 692*b* and the pole shoe 683*b* of the electromagnet unit 690*b*, and air gap 663 on both positive and negative sides of the y axis. Therefore, the bias flux and modulating flux superimpose in the air gaps in between the rotor primary pole piece 673 and the casing pole shoes 683*a*, 683*b*. These fluxes add up in the air gap in between the primary pole piece 673 and the pole shoe 683*b*, on the positive side of the y axis. The bias flux is deducted by modulating flux in the air gap in between the primary pole piece 673 and the pole shoe 683*a*, on the negative side of the y axis. Unbalanced magnetic force on the rotor primary pole piece 673 is thus resulted, pointing to the positive direction in y axis. The magnetic force can be controlled by adjusting the electric current in coil pairs 691*a*, 691*b*. This shows the mechanism of push-pull modulation of bias flux, with which the rotor can be actively controlled by real time adjustment of electric current in electromagnets. In addition, the push and pull effects leads to linearity of control force with respect to control current, as explained above with the other preferred embodiments of this invention.

The bias flux loop 653 and the modulating flux loop 655 take different pathways in three-dimensional space so that they merely overlap in the air gap 663 and its surrounding pole members. The modulating flux does not pass through any permanent magnet, and the bias flux does not pass through any iron core of the electromagnets.

The various aspects of the present invention as discussed above can be used independently or jointly to best address design optimization of a fully magnetically suspended pump for handing stress-sensitive fluids such as blood. Particularly, they are presented to allow the electric motor and magnetic suspension to be adapted to the flow path that is configured to mitigate mechanical stress in fluid, to avoid flow stagnation, and to promote wash out of the fluid-contacting surfaces. Moreover, the electric motor and magnetic suspension are configured in various ways to allow optimization of the pump performances including pump compactness, power efficiency, reliability, suspension stiffness and other dynamic performances of the suspension, among others. In this context, optimization is addressed at the system level rather than components level. Therefore, the present invention should be regarded as a novel pump with the flow path, electric motor, and magnetic suspension configured and integrated in a unified way so that better performance of the entire pump is achieved.

Therefore, according to an aspect of this invention the electric motor and magnetic suspension unit are configured as separate components of the pump, in contrast to some of the conventional magnetically suspended pumps where bearingless motor or combined motor and bearing are employed. The so-called bearingless motor or combined motor and bearing may take various forms but fundamentally features a single rotor assembly serving for both electric motor and magnetic suspension. This is achieved by interaction of one magnetic field of rotor with two groups of coils in stator to respectively create rotational torque of the motor and translational forces of the magnetic suspension. Such a rotor magnetic field may be generated with a plurality of permanent magnets in the rotor and may possess multiple poles. Or, it may be a unipolar magnetic field built on a reluctance rotor that has varying, around the circular periphery, magnetic reluctance of the magnetic circuit energized by permanent magnets or electromagnets in the stator. In general, the rotor of a bearingless motor carries a magnetic field that spatially varies in a regular pattern in circumferential direction. When the rotor rotates, the rotor magnetic field at any point in the air gap varies with time. Although such a variation of rotor magnetic field constitutes a unique characteristic of a bearingless motor, it is to be avoided. In a magnetic suspension construction formed according to one embodiment of the present invention, variation of rotor magnetic field in the air gap when the rotor rotates can cause variations of magnetic force and torque of the magnetic suspension, which acts as an internal disturbance on suspension and thus compromises dynamic performance, e.g. causing vibration. Moreover, since the active suspension of the embodiments of the present invention is based on the mechanism of bias flux modulation, variations of the bias flux with rotational angle of the rotor can lead to unsteady relationship between the control force and current, which can significantly deteriorate control performances including stability robustness, response to external disturbance, suspension stiffness, damping, and so forth. In addition, such a rotor magnetic field can induce eddy current in stator members of electrically conductive material when the rotor rotates, and hampers power efficiency of the entire pump.

Therefore, in contrast to the bearingless motor, the rotor of a magnetic suspension assembly according to an embodiment of the invention is not intended to create regularly varying magnetic field in circumferential direction. Instead, substantially uniform rotor magnetic field for magnetic suspension is preferable. In addition, by separating the electric motor and magnetic suspension, this invention can make better use of available space within pump housing around the specific flow path of this invention, so that the overall pump dimensions can be minimized without compromising the other system performances such as power efficiency and suspension dynamics.

While embodiments of the invention presented herein may describe permanent magnets as annular or ring-shaped, one of skill in the art will recognize that other shapes and configurations of permanent magnets may be implemented to accomplish the desired effect. For example, the permanent magnets may be in the form of annulate segmental magnets.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicants' contribution. The actual scope of the protection sought is intended to be defined in the following claims when viewed in their proper perspective based on the prior art.

The invention claimed is:

1. A pump apparatus, comprising:
a housing having a central axis and an inlet and an outlet adapted to respectively receive and discharge fluid;
a rotor magnetically suspended in the housing and rotatable about the central axis, the rotor having an impeller adapted to pump fluid;
a motor adapted to drive the rotor about a rotational axis substantially coincident with the central axis;
a magnetic suspension device including:
an annular rotor primary pole piece disposed in the rotor coaxially with the rotational axis, the annular rotor primary pole piece including a ferromagnetic material adapted to channel magnetic flux and having first and second end surfaces and a cylindrical side surface adapted to serve as a rotor pole face;
electromagnet units disposed in the housing and circumferentially distributed about the central axis, each electromagnet unit including:
a pole shoe having first and second pole shoe end surfaces and a side pole shoe cylindrical surface adapted to serve as a casing pole face;
a core extending from the pole shoe;
a back yoke connecting the cores of different electromagnet units together; and
a coil wound around the core and adapted to conduct electric current;
wherein the pole shoe, the core, and the back yoke each includes ferromagnetic material adapted to channel magnetic flux;
wherein the first end surface of the rotor primary pole piece and the first end pole shoe surfaces of the pole shoes are on a first side along an axial direction;
wherein the rotor pole face and each of the casing pole faces oppose each other and define a primary suspension gap therebetween, the primary suspension gaps are axially aligned with each other and circumferentially separated from each other;
a permanent magnet adapted to generate bias magnetic fluxes, each of the bias magnetic fluxes radially passing through one of the primary suspension gaps, and passing through the rotor primary pole piece and pole shoe of the electromagnet unit; wherein the permanent magnet is magnetized in such a direction that all the bias magnetic fluxes pass through the primary suspension gaps in a same polar direction;
wherein the electromagnet units are electrically and magnetically coupled to jointly generate a modulating magnetic flux for active control of a position of the rotor along either one of two orthogonal radial axes, a first radial axis having a first side and a second side divided by a second radial axis, the modulating magnetic flux radially passing through a plurality of the primary suspension gaps and superimposing the bias magnetic fluxes to enhance the bias magnetic flux in the primary suspension gap on the first side of the radial axis, and weaken the bias magnetic flux in the primary suspension gap on the second side of the radial axis.

2. The pump apparatus of claim 1, wherein any closed magnetic circuit of the bias magnetic flux passes outside of any core of the electromagnet units.

3. The pump apparatus of claim 1, wherein any closed magnetic circuit of the modulating magnetic flux passes outside of any permanent magnet serving for generation of the bias magnetic flux.

4. The pump apparatus of claim 1, wherein all the bias magnetic fluxes in the primary suspension gaps remain substantially steady when the rotor rotates.

5. The pump apparatus of claim 1, wherein a flow channel between the rotor and the housing allows substantially unimpeded flow to wash out a bounding surface of the flow channel.

6. The pump apparatus of claim 1, wherein the permanent magnet includes one of an annular permanent magnet disposed on one end surface of the rotor primary pole piece, or a pair of annular permanent magnets respectively disposed on both end surfaces of the rotor primary pole piece.

7. The pump apparatus of claim 1, wherein the permanent magnet includes one of an annular permanent magnet disposed on the first end surfaces of the pole shoes, or a pair of annular permanent magnets respectively disposed on both end surfaces of the pole shoes.

8. The pump apparatus of claim 1, wherein the permanent magnet includes a plurality of annulate segmental permanent magnets disposed on the first or the both end surfaces of the pole shoes.

9. The pump apparatus of claim 6, wherein the permanent magnet further includes one of an annular permanent magnet disposed on the first end surfaces of the pole shoes, or a pair of annular permanent magnets respectively disposed on both end surfaces of the pole shoes.

10. The pump apparatus of claim 6, wherein the permanent magnet further includes a plurality of annulate segmental permanent magnets disposed on the first or the both end surfaces of the pole shoes.

11. The pump apparatus of claim 1, further comprising an additional component adapted to provide passive suspension with respect to axial displacement and titling of the rotor; the additional component including:

a first pole piece including one of an annular first pole piece or a plurality of annulate segmental first pole pieces disposed in the rotor and circumferentially distributed at regular intervals about the rotational axis thereof;

a second pole piece including one of an annular second pole piece or a plurality of annulate segmental second pole pieces disposed in the housing and circumferentially distributed at regular intervals about the central axis thereof;

wherein the first and second pole pieces include one of a permanent magnet or a ferromagnetic material adapted to channel magnetic flux, the first and second pole pieces opposing each other along a radial direction;

at least one of the bias magnetic fluxes of the magnetic suspension device passing through the first pole piece and the second pole piece.

12. The pump apparatus of claim 1, wherein the magnetic suspension device includes at least three electromagnet units adapted to generate two groups of the modulating magnetic fluxes, each group respectively serving for active control of the position of the rotor along each of the two orthogonal radial axes.

13. The pump apparatus of claim 12, wherein the magnetic suspension device is adapted to achieve a substantially linear relationship between the electric current fed into a group of the electromagnet units for active control in one radial direction, and a net magnetic force applied on the rotor primary pole piece due to the same electric current.

14. The pump apparatus of claim 1, wherein the magnetic suspension device includes first and second magnetic suspension devices disposed separately along the axial direction; the pump apparatus further comprising:

an annular rotor member including a ferromagnetic material adapted to channel magnetic flux, the annular rotor member connecting the rotor primary pole piece of the first magnetic suspension device with the rotor primary pole piece of the second magnetic suspension device; and one of an annular permanent magnet or annulate segmental permanent magnets, the annular permanent magnet or the annulate segmental permanent magnets disposed between the end surfaces of the pole shoes of the first magnetic suspension device and the end surfaces of the pole shoes of the second magnetic suspension device, wherein the permanent magnet generates the bias magnetic fluxes in the first and second magnetic suspension devices.

15. The pump apparatus of claim 1, wherein the magnetic suspension device includes first and second magnetic suspension devices disposed separately along the axial direction, the pump apparatus further comprising:

a first permanent magnet including an annular first permanent magnet disposed between the end surface of the rotor primary pole piece of the first magnetic suspension device and the end surface of the rotor primary pole piece of the second magnetic suspension device;

a second permanent magnet including one of an annular second permanent magnet or a plurality of annulate segmental second permanent magnets, the second permanent magnet disposed between the end surfaces of the pole shoes of the first magnetic suspension device and the end surfaces of the pole shoes of the second magnetic suspension device;

wherein the first permanent magnet and the second permanent magnet generate the bias magnetic fluxes in the first and the second magnetic suspension devices.

16. The pump apparatus of claim 1, wherein the magnetic suspension device includes first and second magnetic suspension devices disposed separately along the axial direction, the pump apparatus further comprising an additional component adapted to provide passive suspension with respect to axial displacement and tilting of the rotor, the additional component including:

a first pole piece including one of an annular first pole piece or a plurality of annulate segmental first pole pieces disposed in the rotor and circumferentially distributed at regular intervals about the rotational axis thereof;

a second pole piece including one of an annular second pole piece or a plurality of annulate segmental second pole pieces disposed in the housing and circumferentially distributed at regular intervals about the central axis thereof;

wherein the first and second pole pieces include a ferromagnetic material adapted to channel magnetic flux, the first and second pole pieces opposing each other along a radial direction and defining a secondary suspension gap therebetween, the secondary suspension gap disposed between the first magnetic suspension device and the second magnetic suspension device along axial direction;

at least one of the bias magnetic fluxes of the first magnetic suspension device or the second magnetic suspension device passing through the first pole piece and the second pole piece.

17. The pump apparatus of claim 1, wherein the magnetic suspension device includes first and second magnetic suspension devices disposed separately along the axial direction;

wherein the first and second magnetic suspension devices each includes at least two of the electromagnet units adapted for active control of the position of the rotor along a first and a second radial axis respectively, the first and second axes being orthogonal to each other.

18. The pump apparatus of claim 17, wherein the rotor primary pole pieces of the first and of the second magnetic suspension devices are axially separated by one of a non-magnetic material or a permanent magnet that constitutes sufficiently large reluctance to magnetic flux, wherein a crossover of the modulating magnetic fluxes therebetween is substantially zero.

19. The pump apparatus of claim 1, wherein the core of electromagnet unit extends from the pole shoe along a radial direction such that the pole shoes and the back yoke are aligned in the axial direction.

20. The pump apparatus of claim 1, wherein the core of electromagnet unit extends from the pole shoe along a axial direction so that the pole shoes and the back yoke are located on different planes apart from each other along the axial direction.

21. The pump apparatus of claim 1, wherein a flow channel between the rotor and the housing comprises sections joined together in a "U" shaped configuration.

22. The pump apparatus of claim 1, wherein a flow channel between the rotor and the housing comprises sections joined together in a "L" shaped configuration.

23. The pump apparatus of claim 1, wherein the motor includes one of an axial flux motor or a motor adapted to work with a conical air gap, disposed to the side of an axial end of the rotor.

24. The pump apparatus of claim 1, wherein the motor and the magnetic suspension device are disposed separately on an inner and an outer side of the rotor along a radial direction.

25. The pump apparatus of claim 1, wherein the motor is an electric motor having windings wrapped about a non-ferromagnetic core.

26. The pump apparatus of claim 16, further comprising:
- a first rotor member including a ferromagnetic material adapted to channel magnetic flux, the first rotor member connecting the first pole piece with the rotor primary pole piece of the first magnetic suspension device;
- a second rotor member including a ferromagnetic material adapted to channel magnetic flux, the second rotor member connecting the first pole piece with the rotor primary pole piece of the second magnetic suspension device.

27. The pump apparatus of claim 16, further comprising:
- a first permanent magnet connecting the first pole piece with the rotor primary pole piece of the first magnetic suspension device;
- a second permanent magnet connecting the first pole piece with the rotor primary pole piece of the second magnetic suspension device.

* * * * *